(12) United States Patent
Krijger et al.

(10) Patent No.: US 11,464,911 B2
(45) Date of Patent: Oct. 11, 2022

(54) DRUG DELIVERY SYSTEM WITH A DELAY MECHANISM

(71) Applicant: Becton, Dickinson and Company, Franklin Lakes, NJ (US)

(72) Inventors: Peter Krijger, Rockaway, NJ (US); Philip Song, Clifton, NJ (US); Curt Bingham, Hyde Park, UT (US); Stephen C. Simmons, Ringwood, NJ (US); Paul Alchas, Franklin Lakes, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 60 days.

(21) Appl. No.: 16/258,133

(22) Filed: Jan. 25, 2019

(65) Prior Publication Data
US 2019/0151553 A1 May 23, 2019

Related U.S. Application Data

(62) Division of application No. 14/359,069, filed as application No. PCT/US2012/066057 on Nov. 20, 2012, now Pat. No. 10,220,151.
(Continued)

(51) Int. Cl.
*A61M 5/315* (2006.01)
*A61M 5/145* (2006.01)
(Continued)

(52) U.S. Cl.
CPC ........ *A61M 5/31501* (2013.01); *A61M 5/145* (2013.01); *A61M 5/1452* (2013.01);
(Continued)

(58) Field of Classification Search
CPC .. A61M 5/145; A61M 5/1452; A61M 5/1454; A61M 5/1684; A61M 5/20;
(Continued)

(56) References Cited

U.S. PATENT DOCUMENTS 6,620,133 B1  9/2003  Steck
2002/0151855 A1  10/2002  Douglas et al.
(Continued)

FOREIGN PATENT DOCUMENTS

CN         101641125 A     2/2010
WO    WO-2008/112472 A2    9/2009
(Continued)

OTHER PUBLICATIONS

Records from Espacenet showing CN-101641125-A and WO 2008112472 to be publications of the same document. Obtained Aug. 7, 2018.
(Continued)

*Primary Examiner* — Shefali D Patel
(74) *Attorney, Agent, or Firm* — Dickinson Wright PLLC

(57) ABSTRACT

A medicament delivery system, including a medicament container and a delay mechanism that is activated prior to completion of medicament delivery from the medicament container. The delay mechanism automatically activates a subsystem or initiates an operation subsequent to completion of medicament delivery.

9 Claims, 25 Drawing Sheets

Related U.S. Application Data

(60) Provisional application No. 61/562,500, filed on Nov. 22, 2011.

(51) Int. Cl.
  *A61M 5/168* (2006.01)
  *A61M 5/20* (2006.01)
  *A61M 5/32* (2006.01)
  *A61M 5/50* (2006.01)

(52) U.S. Cl.
  CPC ........ *A61M 5/1454* (2013.01); *A61M 5/1684* (2013.01); *A61M 5/20* (2013.01); *A61M 5/2033* (2013.01); *A61M 5/3157* (2013.01); *A61M 5/3158* (2013.01); *A61M 5/321* (2013.01); *A61M 5/5086* (2013.01); *A61M 2005/14506* (2013.01); *A61M 2005/2026* (2013.01); *A61M 2205/276* (2013.01); *A61M 2205/581* (2013.01); *A61M 2205/582* (2013.01)

(58) Field of Classification Search
  CPC ............ A61M 5/2033; A61M 5/31501; A61M 5/3157; A61M 5/3257; A61M 5/326; A61M 5/5086; A61M 2005/14506; A61M 2005/2026; A61M 2005/3265; A61M 2205/27; A61M 2205/273; A61M 2205/276; A61M 5/16804; A61M 5/16813; A61M 5/16881; A61M 5/321; A61M 2005/3128; A61M 2005/3143; A61M 5/3158; A61M 5/31585; A61M 5/3287; A61M 2205/581; A61M 2205/582; A61M 2005/206
  See application file for complete search history.

(56) References Cited

U.S. PATENT DOCUMENTS

| | | |
|---|---|---|
| 2007/0112326 A1 | 5/2007 | Bosshard et al. |
| 2008/0312592 A1 | 12/2008 | Barrow-Williams |
| 2009/0088688 A1 | 4/2009 | Barrow-Williams |
| 2011/0009821 A1 | 1/2011 | Jespersen et al. |
| 2011/0160666 A1 | 6/2011 | Hanson et al. |
| 2012/0010594 A1* | 1/2012 | Holt .................. A61M 5/14248 604/506 |
| 2012/0022499 A1 | 1/2012 | Anderson et al. |
| 2012/0323177 A1 | 12/2012 | Adams |
| 2013/0150801 A1 | 6/2013 | Ekman |

FOREIGN PATENT DOCUMENTS

| | | |
|---|---|---|
| WO | WO-2011/081980 | 7/2011 |
| WO | WO-2011133823 A1 | 10/2011 |

OTHER PUBLICATIONS

English translation of CN-101641125-A. Obtained from Google Patents Aug. 7, 2018.

* cited by examiner

DRUG DELIVERY SYSTEM WITH A DELAY MECHANISM

CROSS-REFERENCE TO RELATED APPLICATION

This application is a division of U.S. Pat. No. 10,220,151, issued on Mar. 5, 2019, which is the U.S. national stage of International Patent Application No. PCT/US2012/066057, filed on Nov. 20, 2012, which claims priority under 35 USC § 119(e) from U.S. Provisional Patent Application Ser. No. 61/562,500, filed on Nov. 22, 2011, the disclosures of which are incorporated herein by reference in their entirety.

BACKGROUND OF THE INVENTION

1. Field of the Invention

The present invention relates to drug or medicament delivery systems, and more particularly, to a drug or medicament delivery system with a delay mechanism.

2. Description of the Related Art

Medicament delivery systems can have multiple subsystem interactions, for example, device activation, valve operation to connect a medicament container with a patient needle, commencement of medicament delivery, needle protrusion, needle withdrawal, and end-of-dose indication. In such medicament delivery systems, each subsystem has a dimensional tolerance. Thus, in the entire device, the accretion of tolerances creates a tolerance window for when the complete dose has been delivered. It is undesirable, for example, to indicate an end-of-dose or withdraw a patient needle prior to the actual dose completion. Accordingly, it would beneficial to have a delay mechanism to ensure dose completion prior to activating such subsystems or operations.

SUMMARY OF EMBODIMENTS OF THE INVENTION

Accordingly, it is an aspect of the present invention to provide a medicament delivery system with a delay mechanism to ensure dose completion prior to activation of at least one subsystem or operation.

The foregoing and/or other aspects of the present invention are achieved by providing a medicament delivery system, including a medicament container and a delay mechanism that is activated prior to completion of medicament delivery from the medicament container. The delay mechanism automatically activates a subsystem or initiates an operation subsequent to completion of medicament delivery.

The foregoing and/or other aspects of the present invention are also achieved by providing a method of delivering a medicament, the method including receiving an activation command, and in response to receiving the activation command, releasing an ejection mechanism to eject medicament from a container. The method also includes, prior to ejecting substantially all the medicament from the container, activating a delay mechanism, and subsequent to ejecting substantially all of the medicament from the container, automatically activating a subsystem or initiating an operation via the delay mechanism.

Additional and/or other aspects and advantages of embodiments of the present invention will be set forth in the description that follows, or will be apparent from the description, or may be learned by practice of the invention.

BRIEF DESCRIPTION OF THE DRAWINGS

The above and/or other aspects and advantages of embodiments of the invention will become apparent and more readily appreciated from the following detailed description, taken in conjunction with the accompanying drawings, in which.

DETAILED DESCRIPTION OF EMBODIMENTS OF THE PRESENT INVENTION

Figure 1:
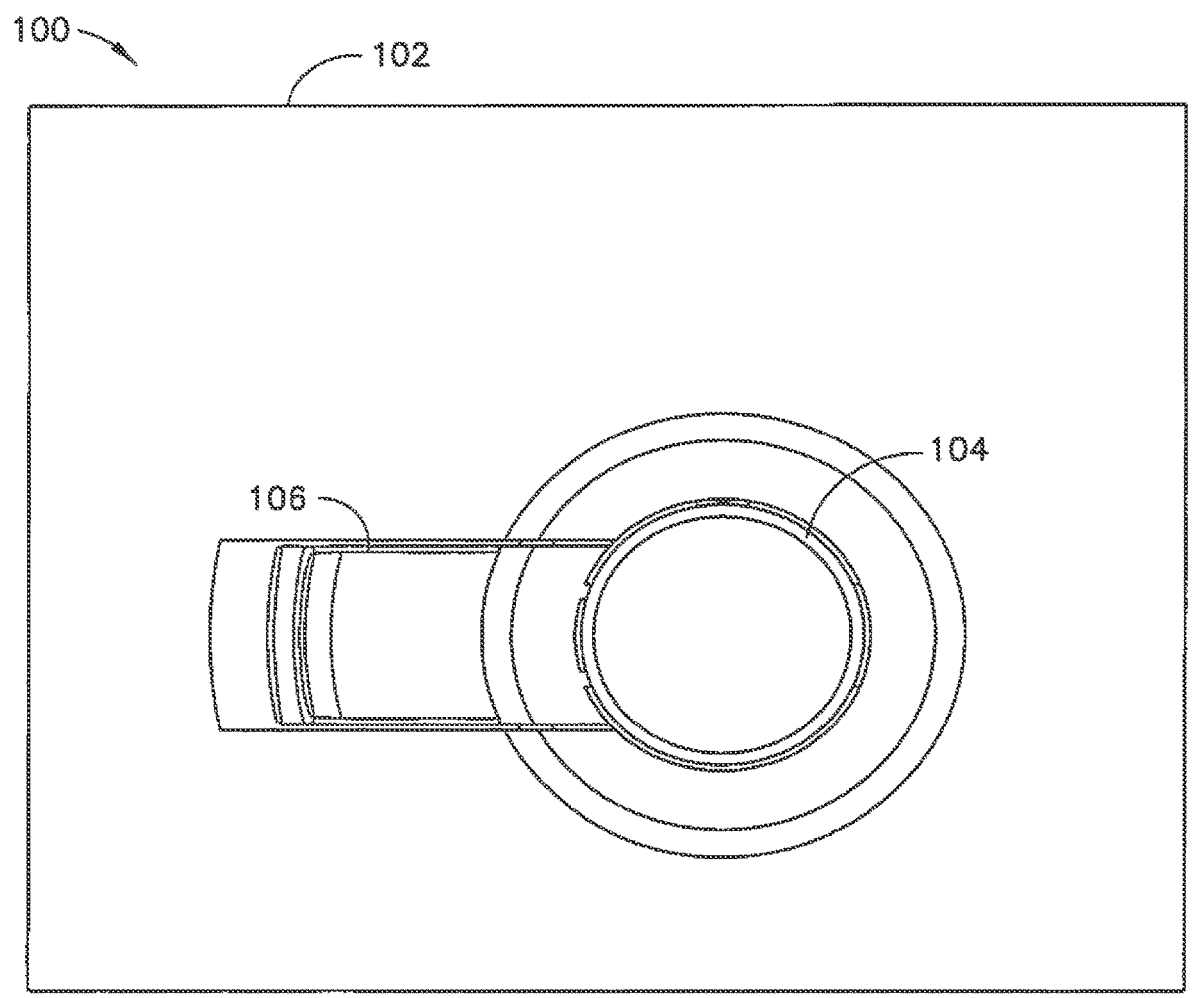
FIG. 1 is a top perspective view of a medicament delivery device in accordance with an embodiment of the present invention.
Figure 2:
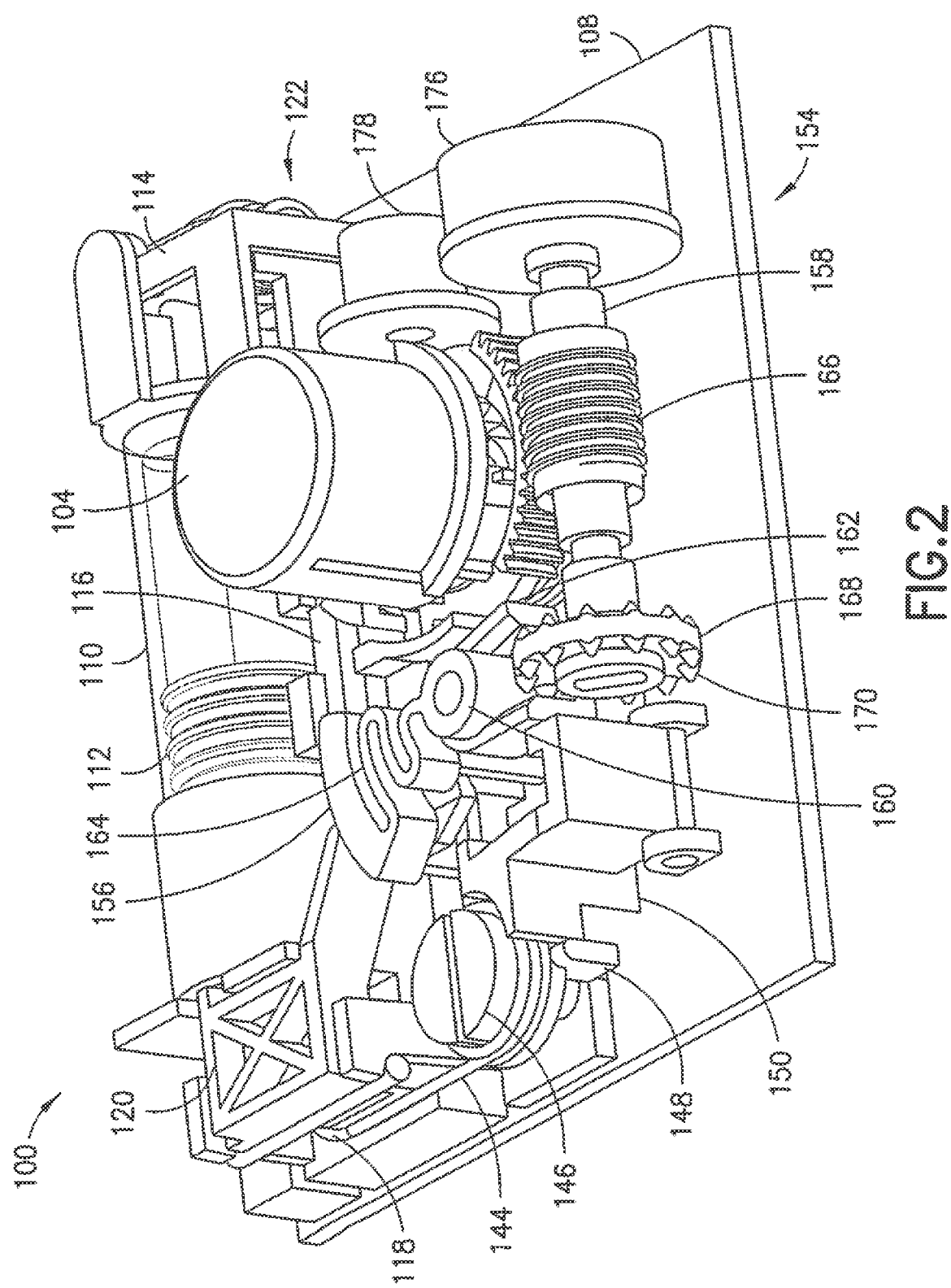
FIGS. 2 and 3 are perspective views of the interior of the device of FIG. 1 illustrating the operation thereof.

Reference will now be made in detail to embodiments of the present invention, which are illustrated in the accompanying drawings, wherein like reference numerals refer to like elements throughout. The embodiments described herein exemplify, but do not limit, the present invention by referring to the drawings. As will be understood by one skilled in the art, terms such as up, down, bottom, and top are relative, and are employed to aid illustration, but are not limiting.

FIG. 1 is a top perspective view of a medicament delivery device 100 in accordance with an embodiment of the present invention. The device 100 includes a main body 102, an activation button 104, and a safety 106. To operate the device 100, the user first slides the safety 106 away from the activation button 104 to disengage the safety 106 from the activation button 104. At this stage, subsequent to placing the device 100 on the patient's skin, the user can depress the activation button 104 to begin the process of medicament delivery. It will be understood by those skilled in the art that the user and the patient may be different people, or that the user and the patient may be the same person. The terms "user" and "patient" will sometimes be used interchangeably hereinafter. It will be understood that embodiments of the invention are not limited to those in which the user and the patient are the same person or to those in which the user and the patient are different people.

FIGS. 2, 3, and 6-9 are perspective views of the interior of the device 100 illustrating the operation thereof. The device 100 includes a base 108, a liquid medicament container 110 with a stopper 112 movably disposed therein, and, as will be subsequently described in greater detail, a delay mechanism that is automatically activated prior to completion of medicament delivery. The delay mechanism automatically activates a subsystem or initiates an operation subsequent to completion of medicament delivery.

The device 100 also includes a valve 114, a sliding bracket 116, a biased plunger 118 for displacing the stopper 112 within the medicament container 110 to dispense the medicament, and a shutter 120 for selectively retaining and releasing the plunger 118. According to one embodiment, the device 100 additionally has an injection/retraction column assembly 122, which includes the activation button 104.

Figure 3:
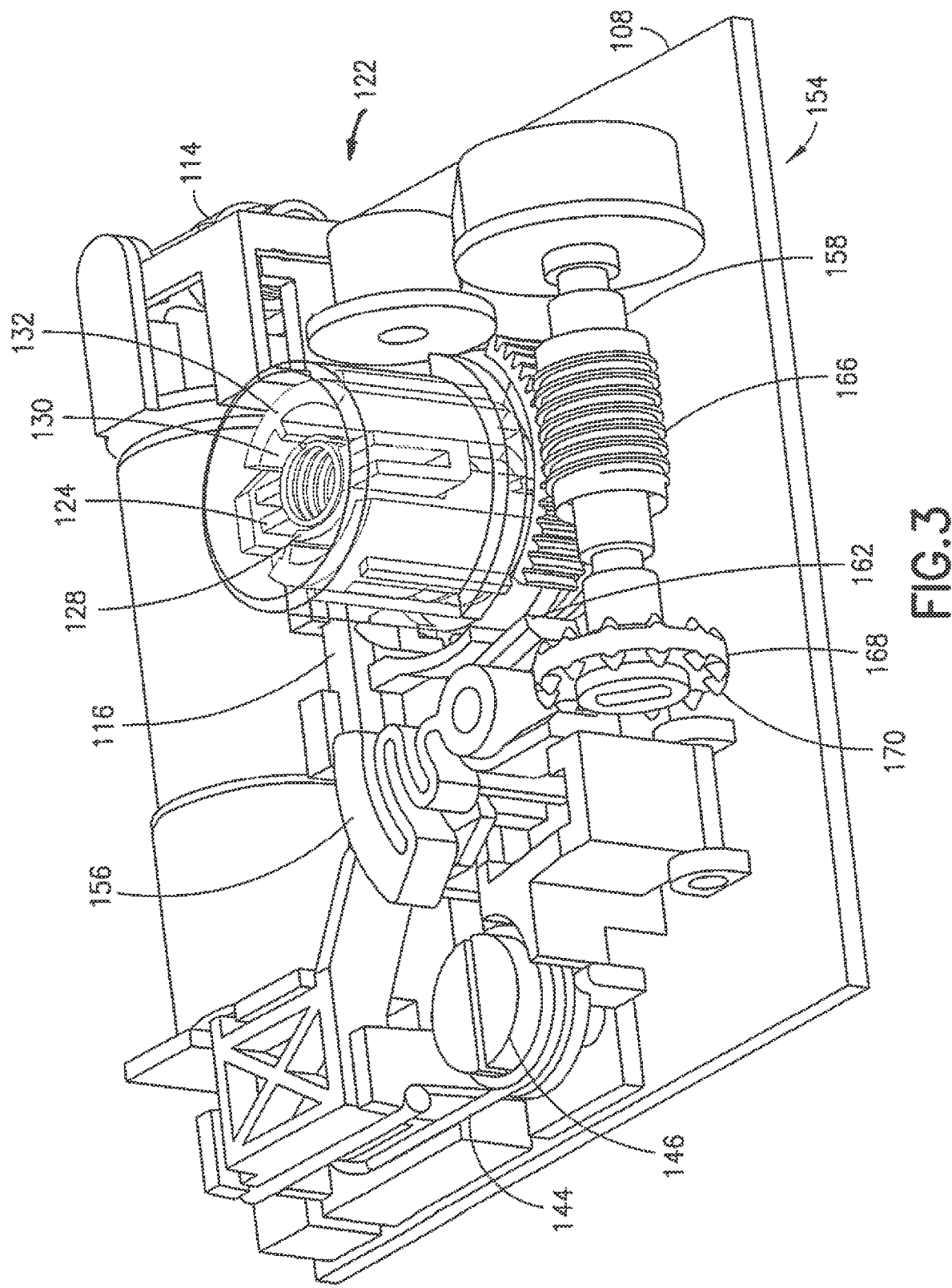
Figure 4:
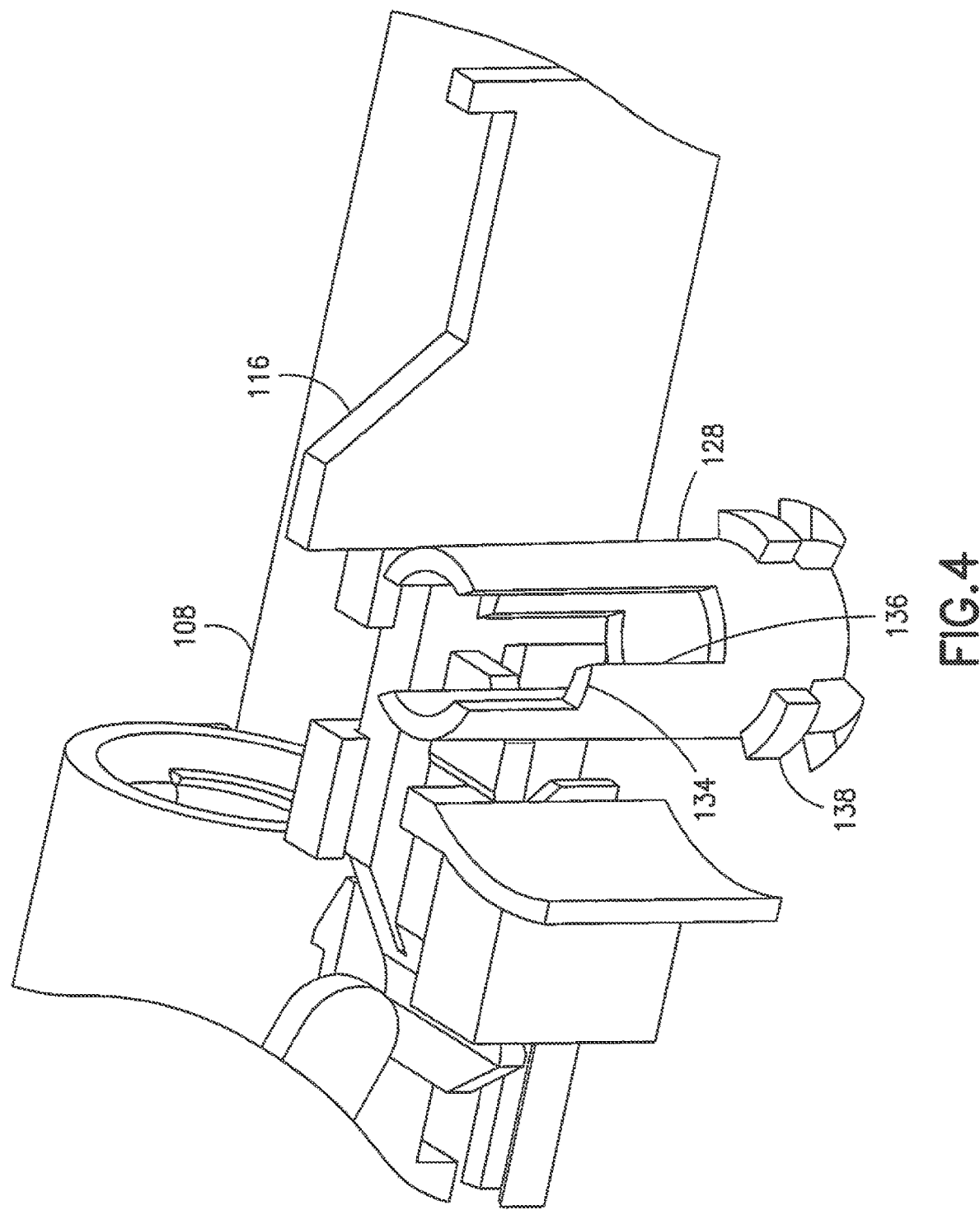
FIG. 4 is a partial perspective view of a column base of the device of FIG. 1.
Figure 14:
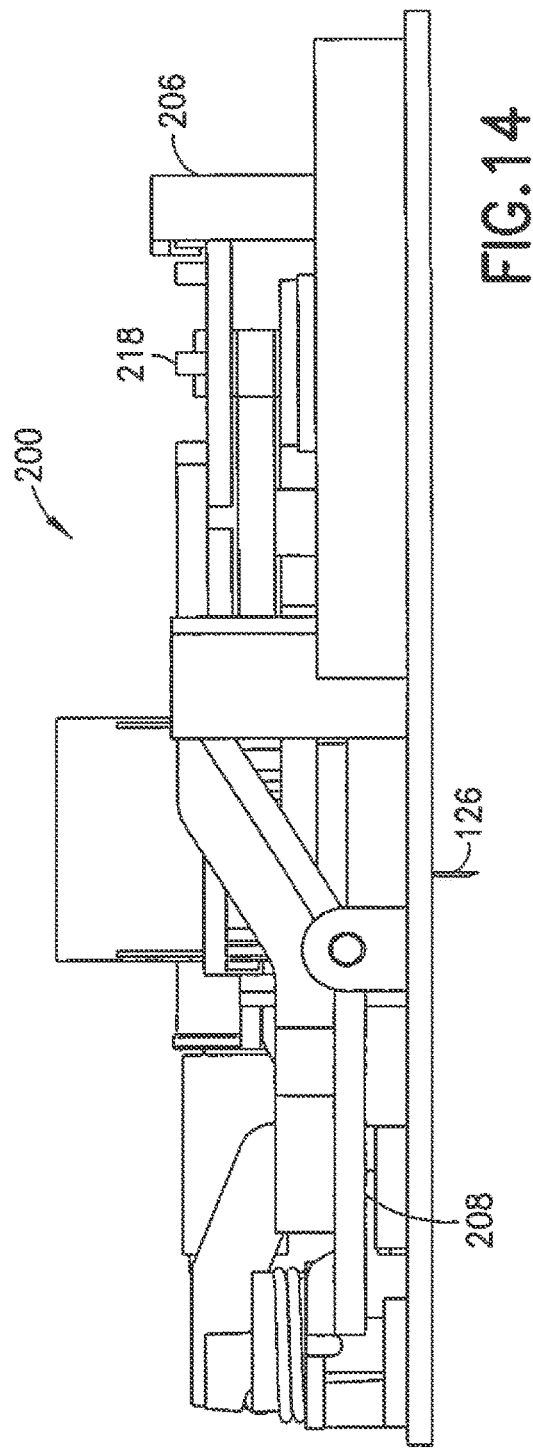
FIGS. 14 and 15 are side perspective view of the device of FIG. 12 illustrating the activation of a delay mechanism.
Figure 15:
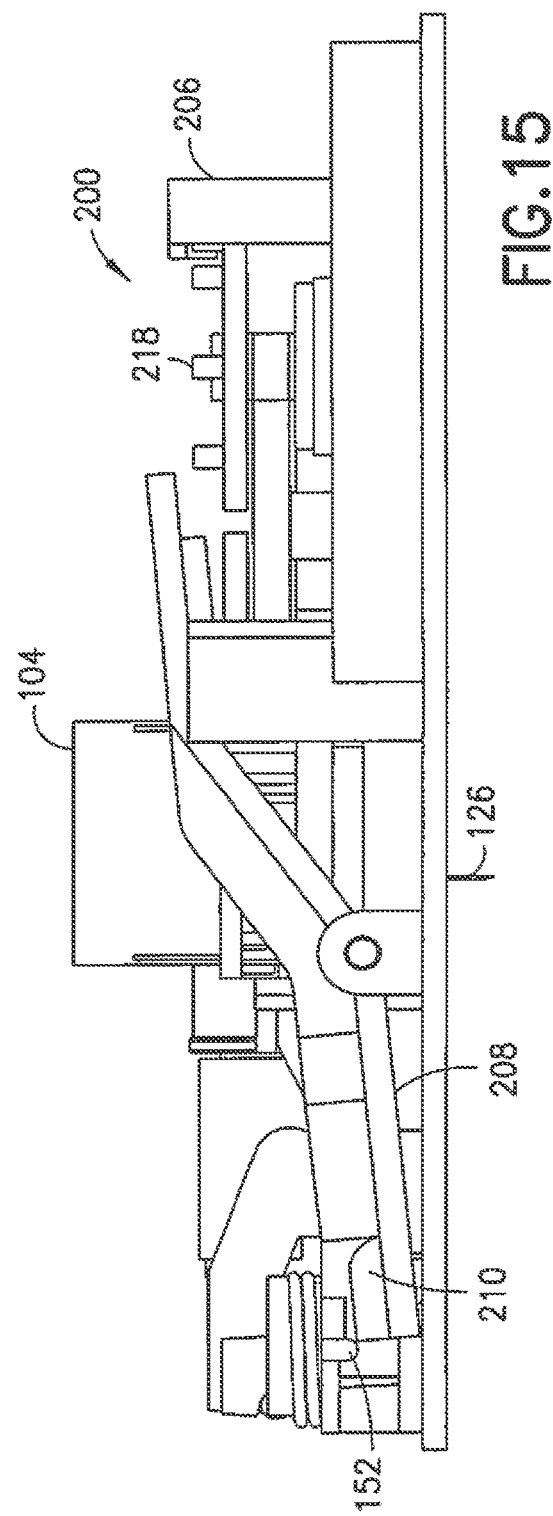

As shown, in FIG. 3, in which the activation button 104 is illustrated as being transparent, the column assembly 122 also includes a needle arbor 124 in which a patient needle 126 (shown, e.g., in FIGS. 14 and 15) is disposed, a column base 128, a needle spring 130 biasing the needle arbor downward, and a column member 132. According to one embodiment, the column base 128 is integrally formed as a unitary structure with the base 108. According to another embodiment, the column base 128 is attached to the base 108. As shown in FIG. 4, the column base 128 includes a guide surface 134 for guiding rotation of the needle arbor 124, and a guide portion 136 for guiding vertical displacement of the needle arbor 124 to extend the needle 126 beyond the base 108 for insertion into the user. In addition, multiple retaining portions 138 are disposed about the column base 128.

Figure 5:
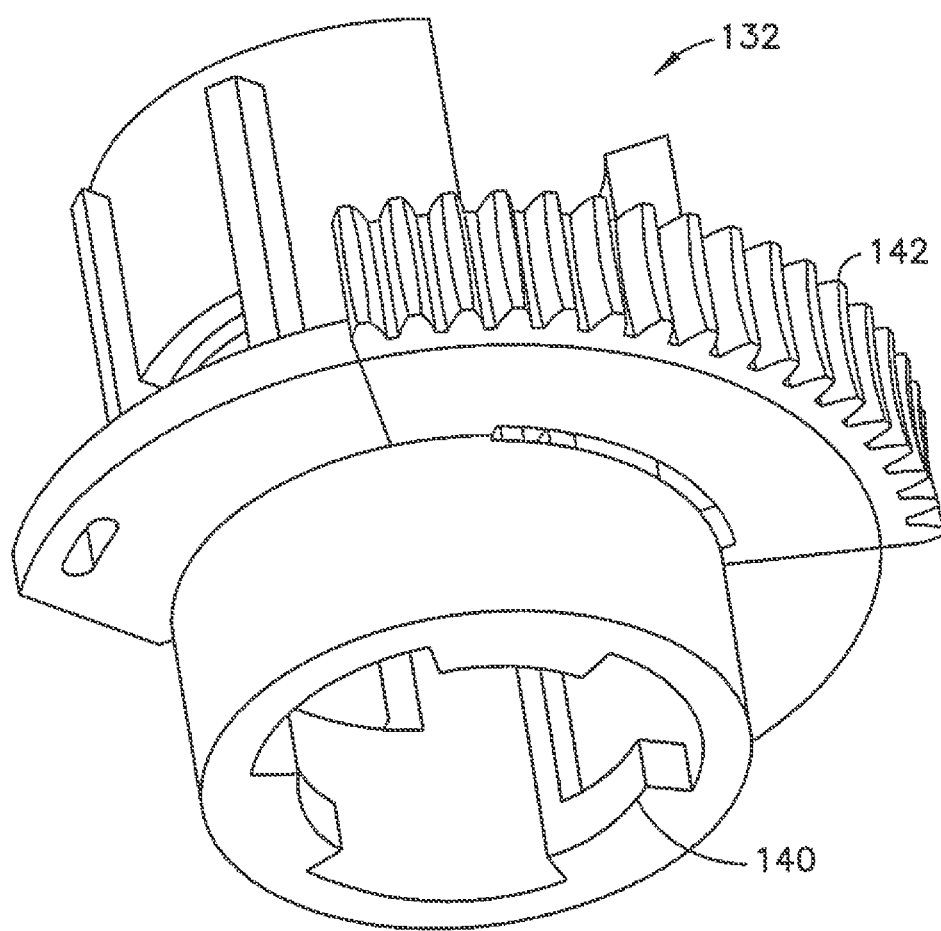
FIG. 5 is a perspective bottom view of a column member of the device of FIG. 1 Fig.
Figure 6:
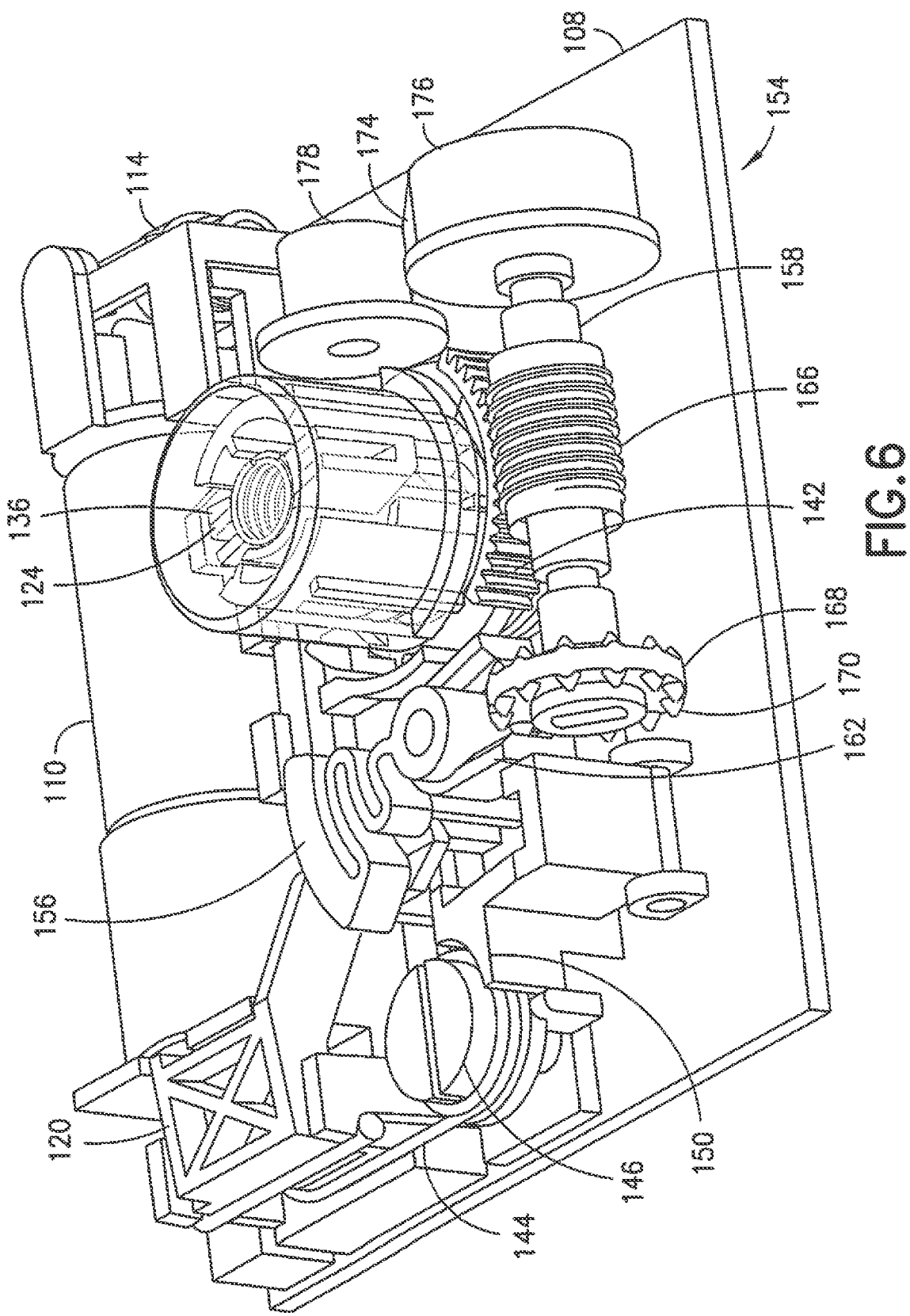
FIGS. 6-9 are perspective views of the interior of the device of FIG. 1 illustrating the operation thereof.

As subsequently discussed in greater detail, the retaining portions 138 interact with feet 140 of the column member 132, which is shown in FIG. 5. The column member 132 also includes a gear portion 142 for interfacing with the delay mechanism.

Figure 7:
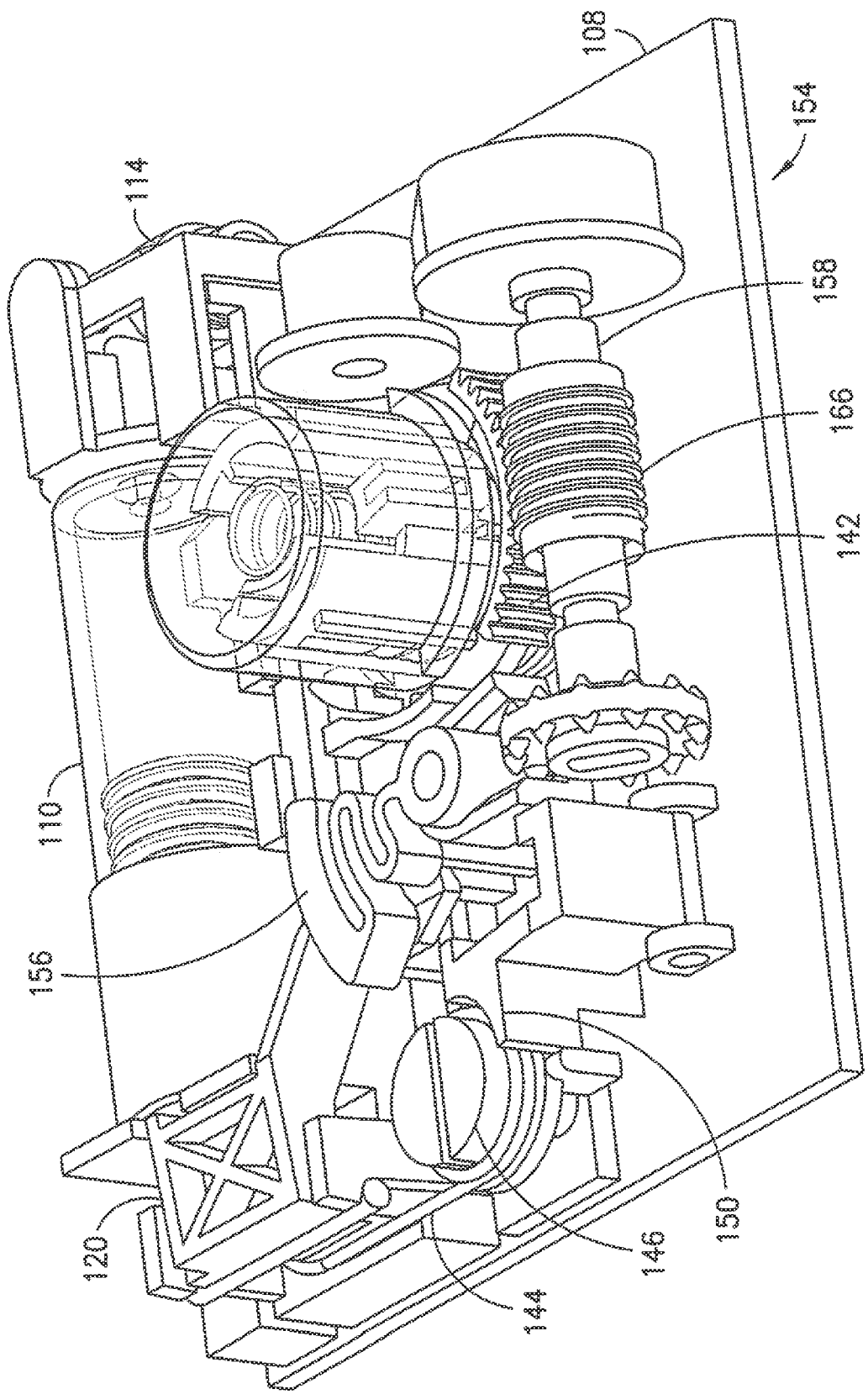

In operation of the device 100, after displacing the safety 106, the action of depressing the activation button 104 (the state illustrated in FIG. 3) releases the biased sliding bracket 116. The sliding motion of the sliding bracket 116 rotates the needle arbor 124 until the arms of the needle arbor 124 reach the guiding portion 136 (FIG. 6), at which point the needle spring 130 displaces the needle arbor 124 downward along the guiding portion 136 to displace the needle 126 outside of the device 100 and into the user (FIG. 7). The sliding motion of the sliding bracket 116 also opens the valve 114 (FIG. 8) and activates the shutter 120 (FIGS. 6-8), which releases the biased plunger 118 to begin displacing the stopper 112 within the medicament container 110.

As noted previously, the collective tolerances of the various components of a medicament delivery device may affect the time required to deliver a complete dose. For example, the length of the stopper, the inner diameter of the medicament container, the inner diameter of the needle, and the inner diameter of the connection between the medicament container and the needle, may all affect the flow rate of the medicament, and thus the amount of time required to complete delivery of the dose.

Because of the expense of some medicaments, users want delivery of substantially 100% of the dosage, and may want an indication of when the dose has been delivered. But because of the collective tolerances of the various components, the certainty of dose completion may be difficult to determine, particularly if the dose is administered over a relatively long period of time, such as 5, 10, 20, or 60 minutes. For example, if the collective tolerances of the various components yields 10% variability in the rate of dosage delivery, with a target dosage delivery time of 60 minutes, the dose could be delivered in 54 minutes or 66 minutes. Accordingly, it is desirable to have a delay mechanism to activate one or more post-delivery subsystems or operations, such as valve closure, end-of-dose indication, or needle protection. Such a delay mechanism can be triggered, for example, at 90 or 95% of dose completion, and then, after the predetermined delay, which would ensure dose completion, the delay mechanism can activate the subsystem or initiate the operation.

According to one embodiment, the plunger 118 includes a tail portion 144 that is wrapped around a spool 146, which includes a spool arm 148. As the plunger 118 displaces the stopper 112 within the medicament container 110, the tail portion 144 unwinds from the spool 146, thereby rotating the spool 146 and the spool arm 148. After a predetermined displacement of the plunger 118 and stopper 112, and a corresponding amount of rotation of the spool 146, the spool arm 148 engages a delay actuator 150, which activates the delay mechanism. According to one embodiment, the spool arm 148 engages a cam surface 152 (best shown in FIG. 11) of the delay actuator 150 to rotate the delay actuator 150 out of engagement with a pallet member.

As shown in FIGS. 2, 3, and 6-9, a delay mechanism 154 includes a biasing mechanism. According to one embodiment, the biasing mechanism includes a spring 174 wound between two spools 176 and 178 (see, e.g. FIG. 6). Spool 176 is concentrically disposed with a shaft 158 to rotate therewith. The delay mechanism 154 also includes a pallet member 156 and a shaft 158. The pallet member 156 includes a base portion 160 and a pair of opposing pallet arms 162 extending from the base portion 160. The base portion 160 is rotatably connected to the base 108. According to one embodiment, the base portion 160 is biased to a neutral position. To accomplish this neutral bias, the pallet member 156 includes a biasing portion 164 (see, e.g. FIG. 2).

The shaft 158 includes a worm gear 166 that engages the gear portion 142 of the column member 132. The shaft 158 also includes an impulse wheel or disc 168 having teeth or cogs 170 circumferentially disposed on opposing sides thereof for interacting with the pallet arms 162.

Once the spool arm 148 engages the cam surface 152 of the delay actuator 150 to rotate the delay actuator 150 out of engagement with the pallet member 156, thereby activating the delay mechanism 154, the pallet member 156 is free to oscillate about its rotational axis. Because of the bias of spring 174, the shaft 158 rotates, thereby causing teeth 170 on opposing sides of the wheel 168 to alternately engage the pallet arms 162. This interaction delays rotation of the shaft 158.

Figure 8:
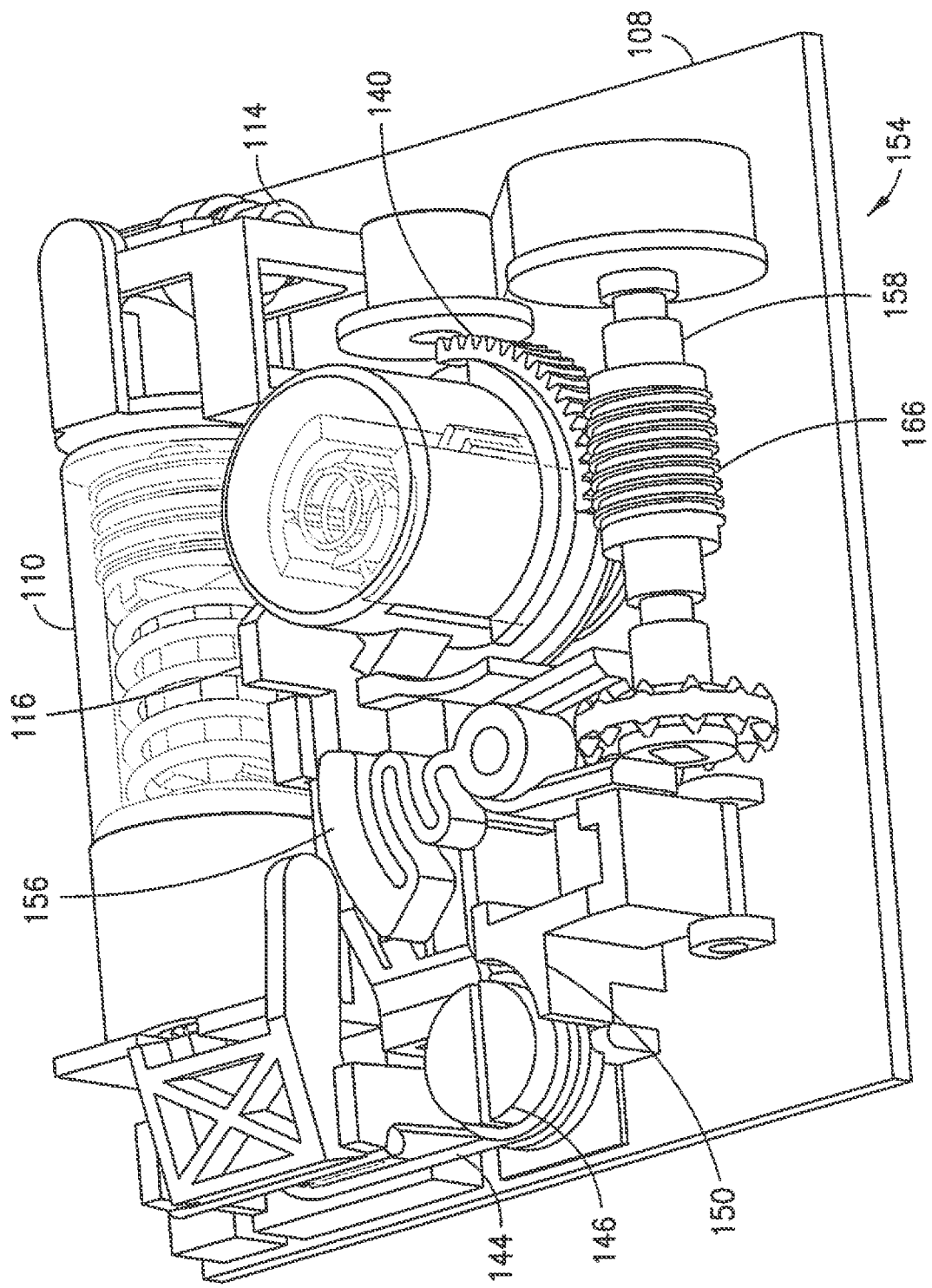
Figure 9:
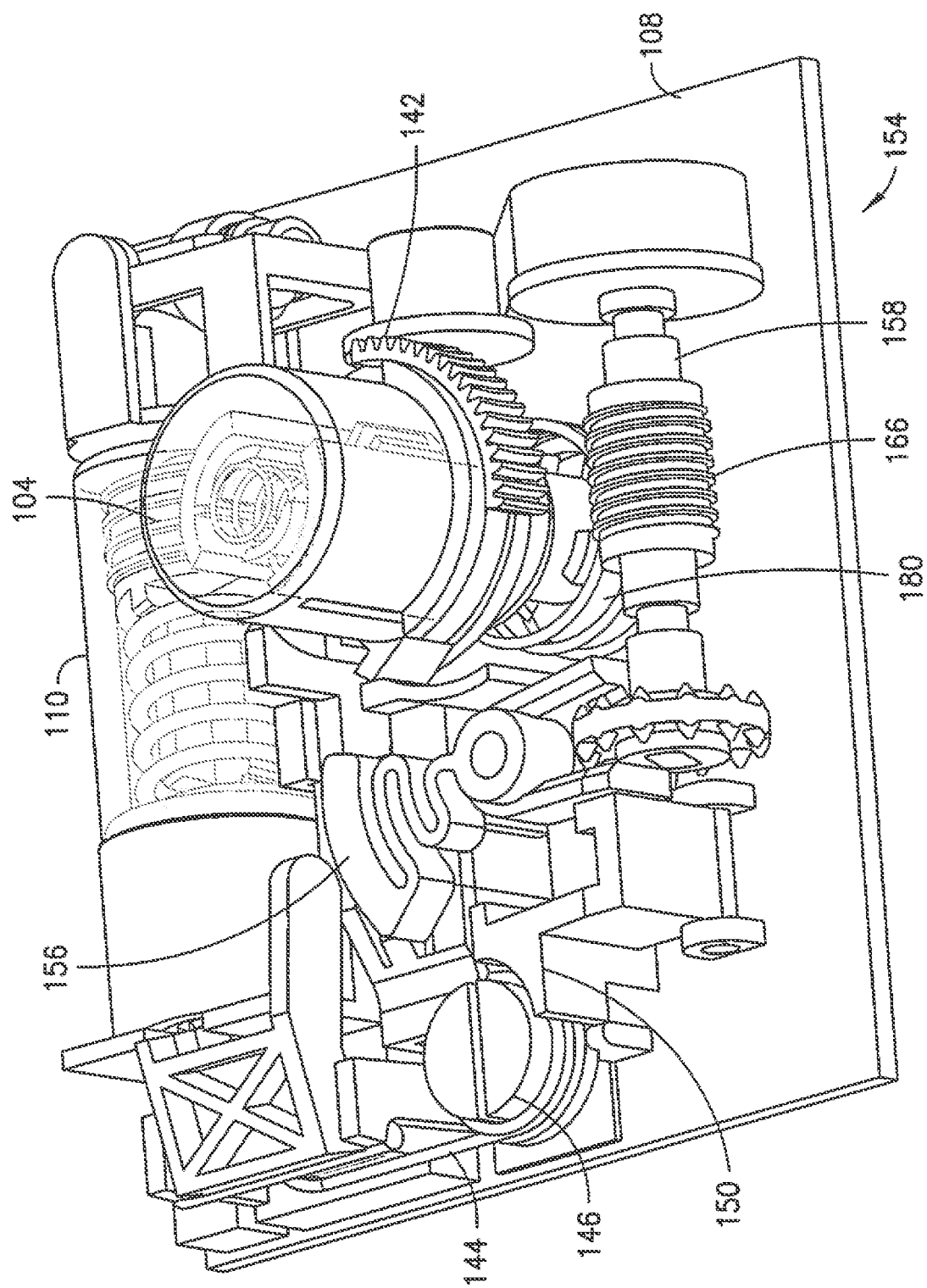

The rotation of the shaft 158 also rotates the worm gear 166, which, because of its interaction with the gear portion 142, causes the rotation of the injection/retraction column assembly 122, as shown in FIG. 8. Subsequent to a predetermined amount of rotation of the column assembly 122, which occurs subsequent to the completion of medicament delivery, feet 140 of the column member 132 no longer align with the retaining portions 138 of the column base 128, and a column spring 180 displaces the column assembly 122 upward, away from the user (FIG. 9). This column assembly displacement withdraws the needle from the user's skin and back within the device 100. Thus, according to one embodiment, the delay mechanism 154 automatically activates a subsystem (the needle safety mechanism) subsequent to completion of medicament delivery. Additionally, because of the location of the activation button 104 on the column assembly 122, when the column assembly 122 moves upward, the activation button 104 also moves upward, thereby serving as a visual end-of-dose indicator. Further, according to one embodiment, the upward movement of the column assembly 122 serves as an audible and tactile feedback indicating dosage completion.

Several factors can be designed to affect the total delay of the delay mechanism 154. For example, the length of the tail 144, the diameter of the spool 146, and the initial angular position of the spool arm 148. Additional factors include the number, size, and shape of the teeth 170, the diameter of the disc 168, how quickly the pallet member 156 oscillates (i.e. length of pallet arms 162 and/or strength of biasing element 164), and how powerful the spring 174 is.

Figure 10:
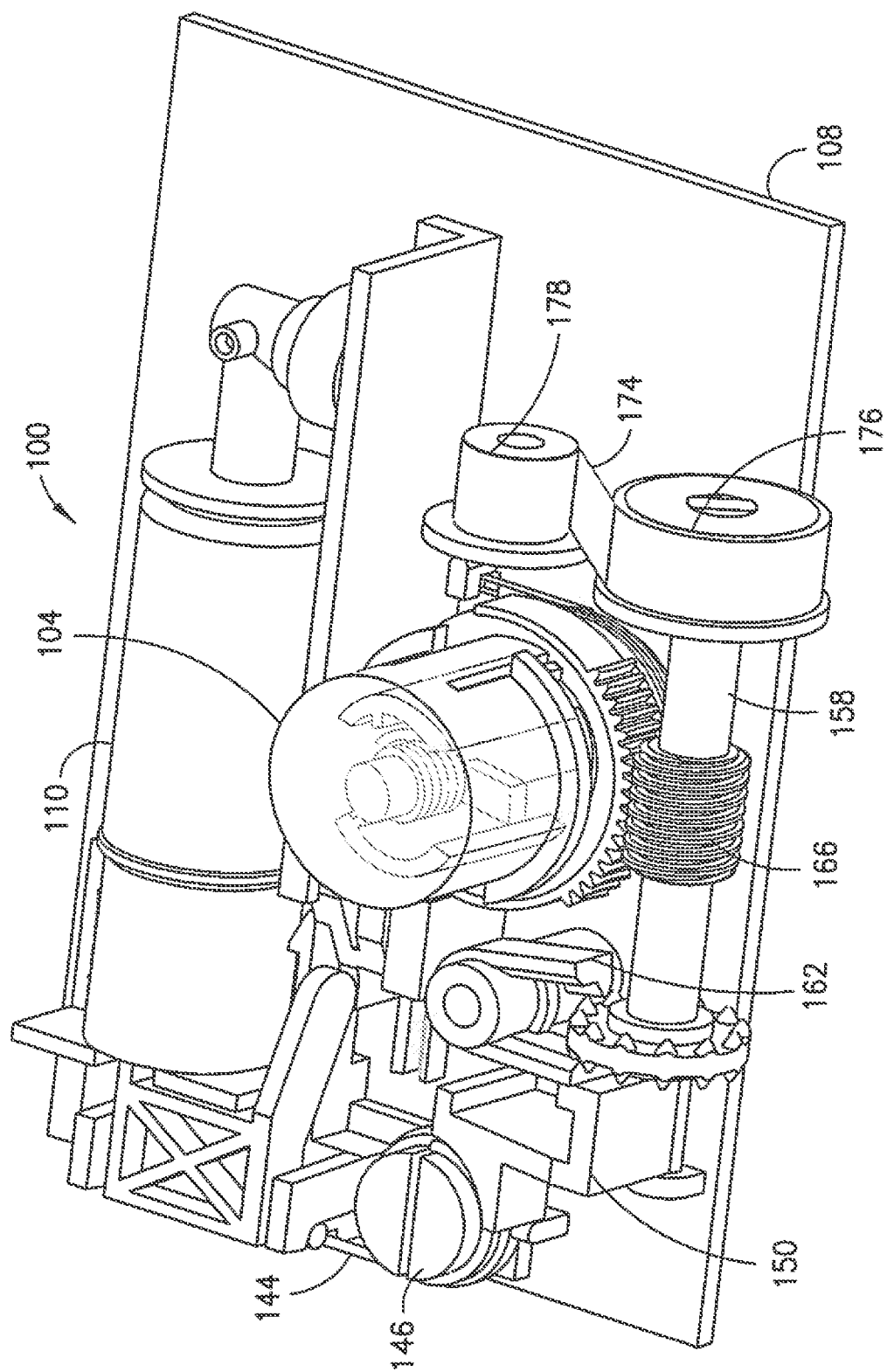
FIGS. 10 and 11 are partial perspective views of the device of FIG. 1 illustrating an alternative pallet member.
Figure 11:
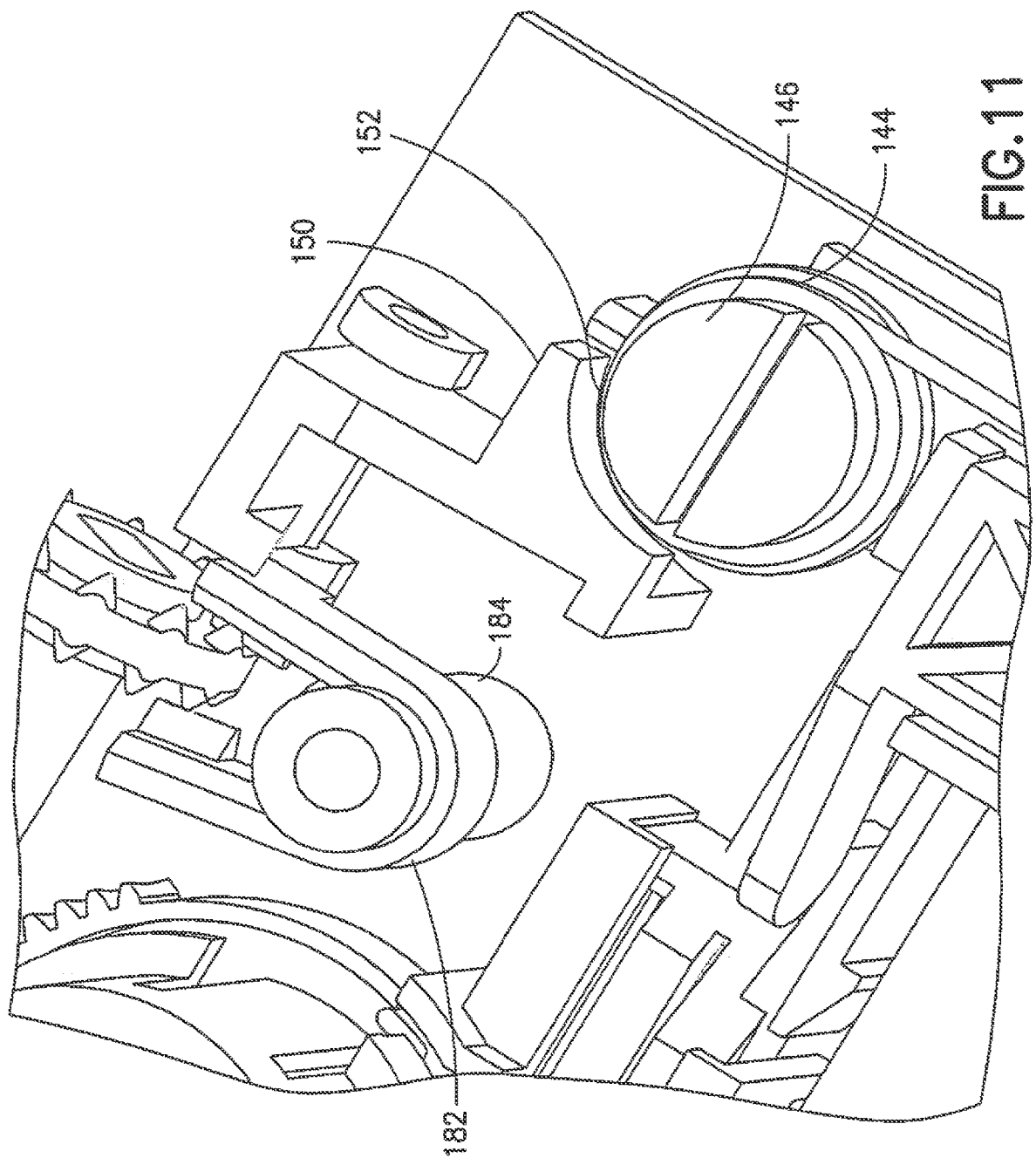

FIGS. 10 and 11 are partial perspective views of the device of FIG. 1 illustrating an alternative pallet member. In this embodiment, rather than the biasing portion 164, the pallet member 182 includes one or more springs inside a central column 184. This internal spring biases the pallet member to the neutral position.

Figure 12:
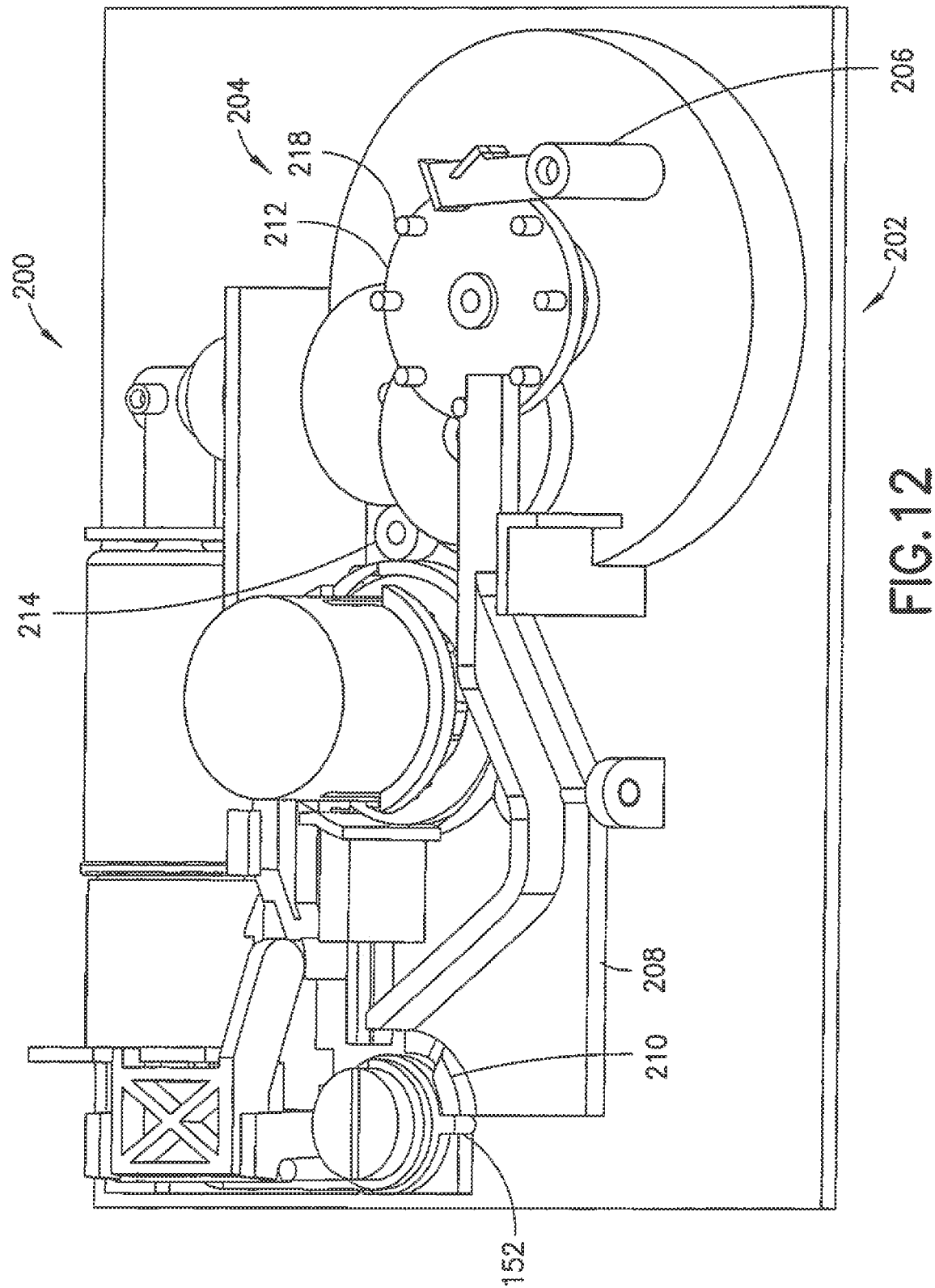
FIGS. 12 and 13 are a partial perspective views of a medicament delivery device in accordance with another embodiment of the present invention.

FIG. 12 is a partial perspective view of a medicament delivery device 200 in accordance with another embodiment of the present invention. In many respects, the device 200 functions substantially similarly to the previously-described device 100. Accordingly, for brevity, redundant description is omitted. The device 200 employs a delay mechanism 202 that includes a plurality of intermeshing gears 204 and a rocking arm 206 having a plurality of paddles or blades thereon. In this embodiment, the delay actuator 208 includes a pivoting arm 208 having a cam surface 210 at a first end thereof for interacting with the spool arm 152. A second, opposing end of the pivoting arm 208 initially engages a cog gear 212 (FIGS. 12-14) to prevent rotation of the gears 204.

Figure 13:
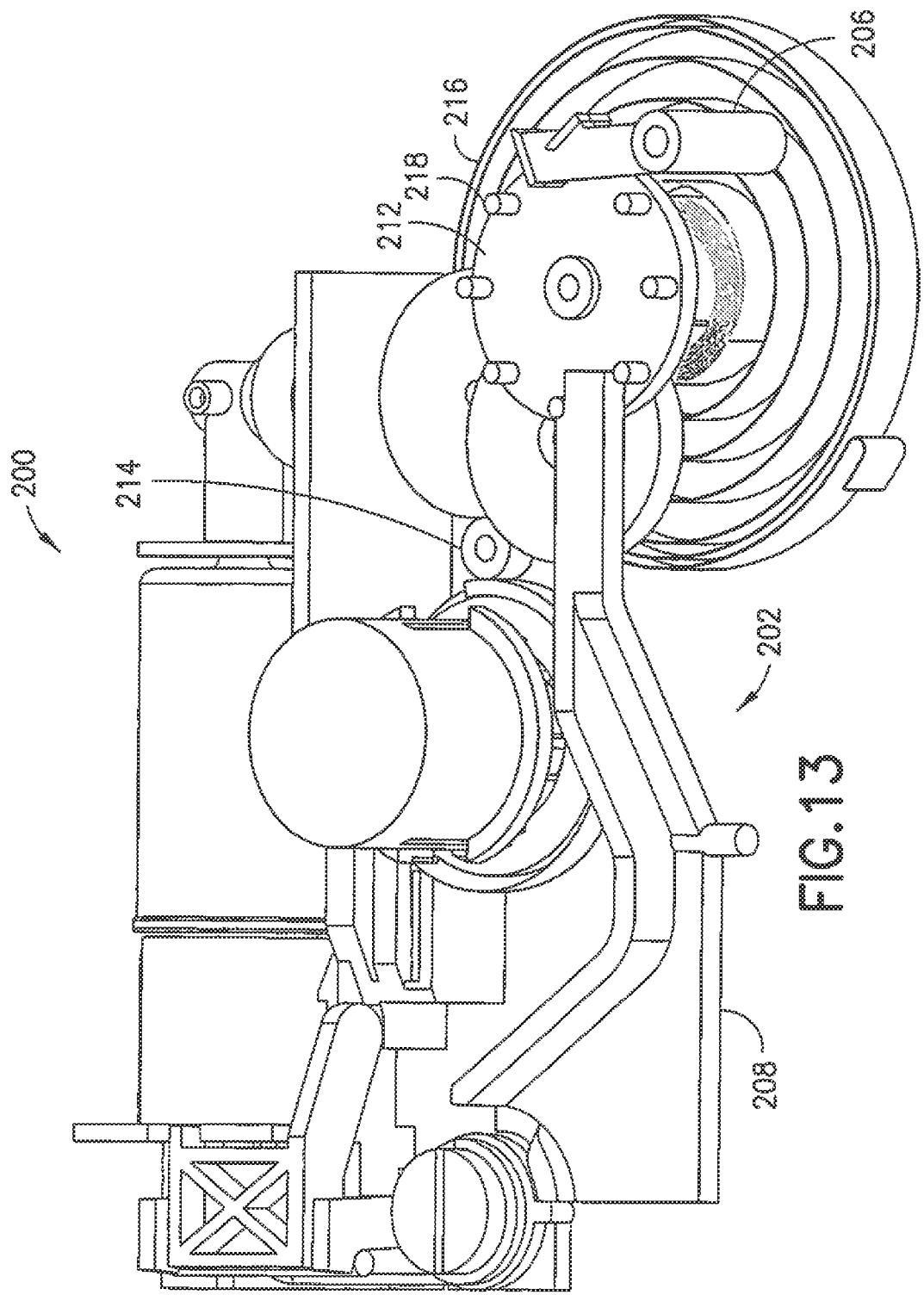

The gears 204 also include an interface gear 214 that interfaces with the gear portion 142 to selectively rotate the column assembly 122. Additionally, as shown in FIG. 13, the gears 204 are biased by a biasing member 216, such as a clock spring 216. One skilled in the art will appreciate that other biasing members can be employed without departing from the scope of the present invention.

The cog gear 212 has a plurality of cogs 218 that interact with both the pivoting arm 208 and the rocking arm 206. In operation, prior to completion of the medicament dose, once the spool arm 152 rotates over the cam surface 210 to pivot the pivoting arm 208 out of contact with the cog 218 of the cog gear 212 (FIG. 15), the cog gear 212 (and the remaining intermeshed gears) begins to rotate under the influence of the biasing member 216. As the cog gear rotates, successive cogs 218 slidingly engage alternating ones of the paddles 220 of the rocking arm 206.

This interaction of the escapement mechanism delays the rotation of the gears 204, so that, subsequent to the completion of the medicament dosage, the column assembly 122 rotates until the feet 140 of the column member 132 no longer align with the retaining portions 138 of the column base 128, and the column spring 180 displaces the column assembly 122 upward. Thus, the delay mechanism 202 automatically activates a subsystem (the needle safety mechanism and/or the end-of-dose indicator) subsequent to completion of medicament delivery.

Figure 16:
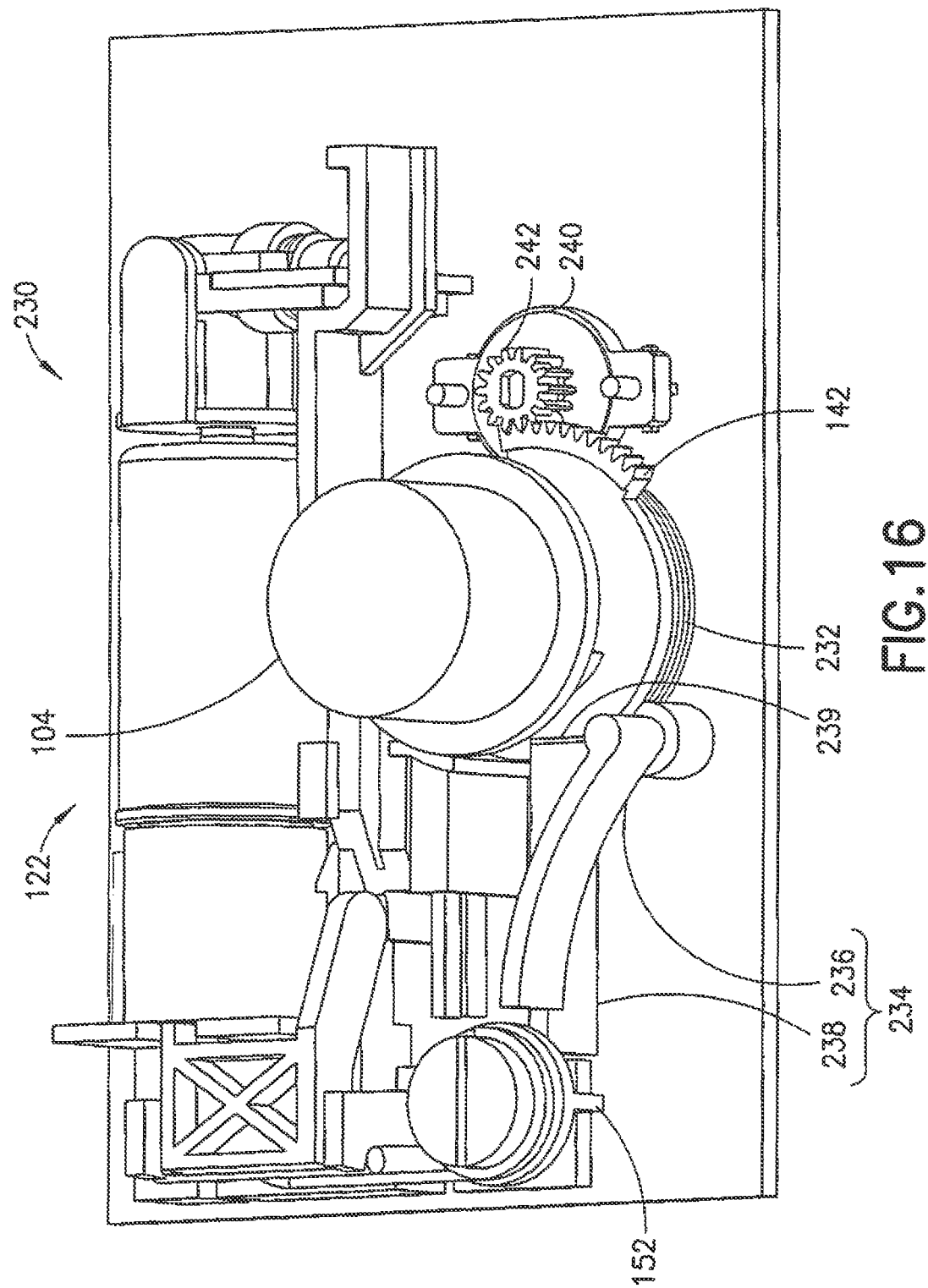
FIGS. 16-18 are partial perspective views of a medicament delivery device in accordance with another embodiment of the present invention.
Figure 17:
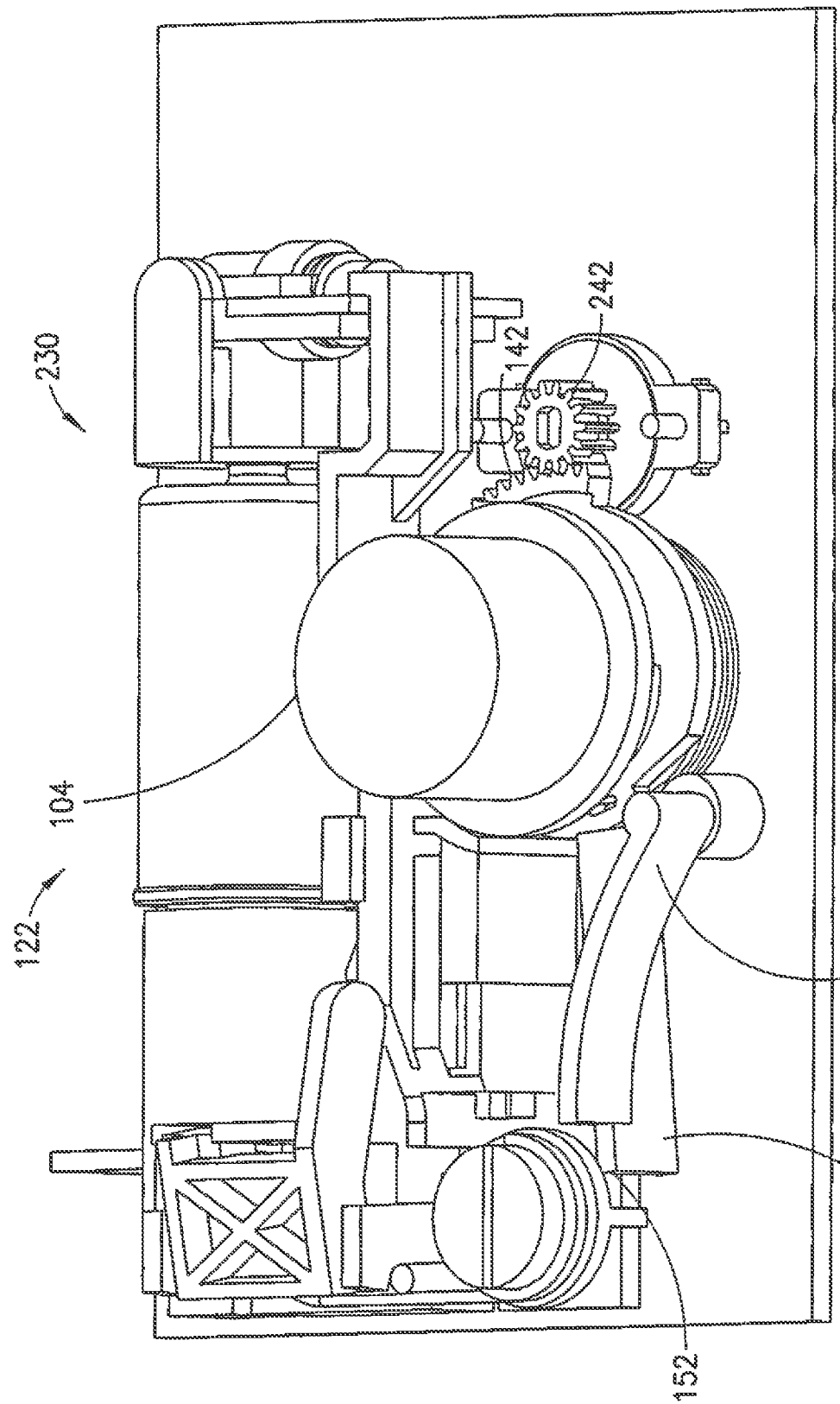
Figure 18:
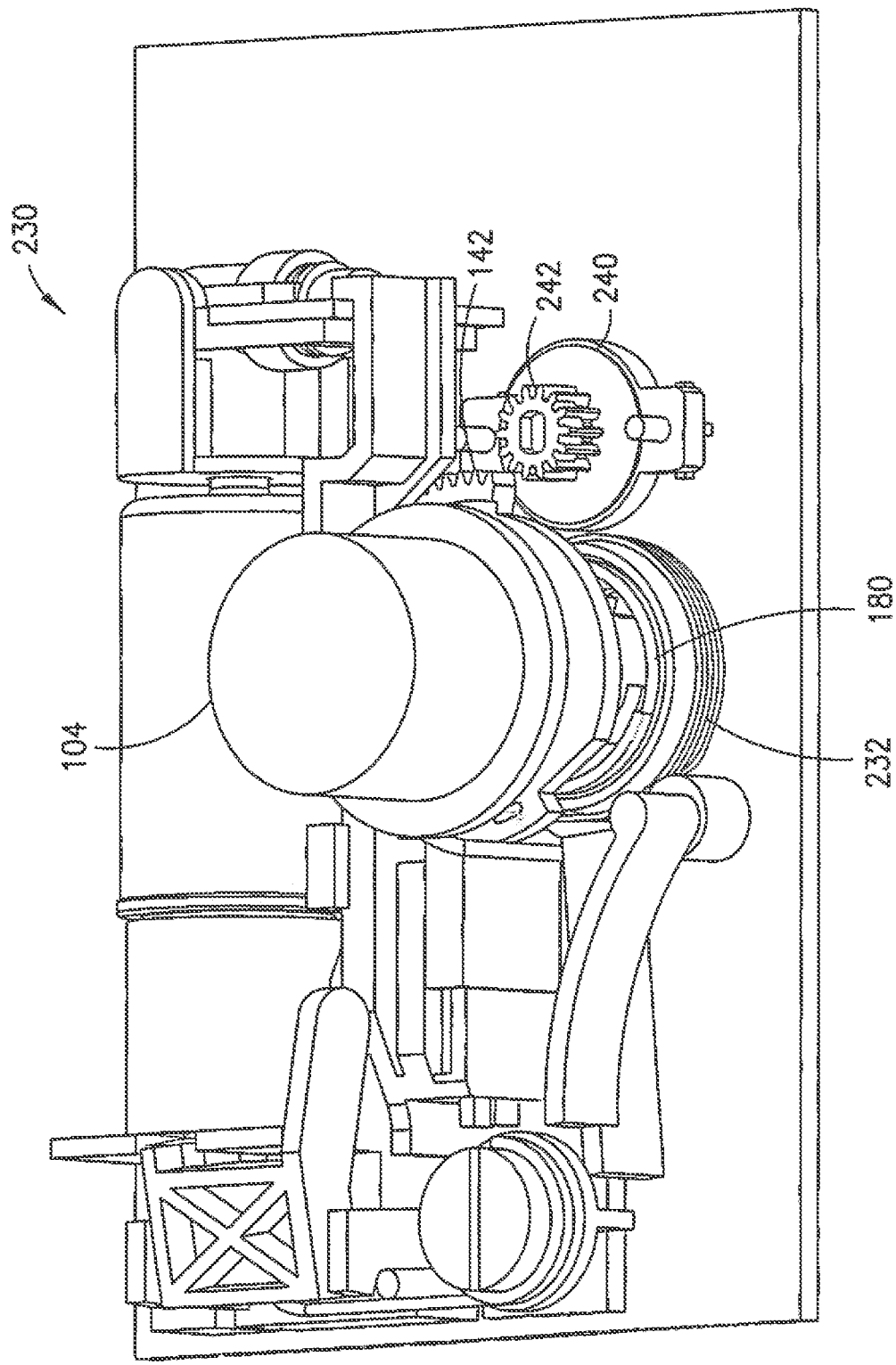

FIGS. 16-18 are partial perspective views of a medicament delivery device 230 in accordance with another embodiment of the present invention. In many respects, the device 230 functions substantially similarly to the previously-described device 100. Accordingly, for brevity, redundant description is omitted. In addition to the column spring 180 biasing the column assembly 122 upward, the column assembly 122 includes a column torsion spring 232 rotatably biasing the column assembly 122.

In this embodiment, the delay activator 234 includes a rotating arm portion 236 and an engaging portion 238. The engaging portion 238 has a first end for selective engagement with the spool arm 152 and a second, opposing end for selective engagement with a notch 239 in the column assembly 122. As shown in FIG. 16, the engaging portion engages the notch 239 to selectively prevent rotation of the column assembly 122.

The device 230 also includes a delay mechanism including a dampener cartridge 240 with a gear 242 thereon for engagement with the gear portion 142. According to one embodiment, the dampener cartridge 240 includes a viscous fluid, such as silicone, that is pushed through openings when the gear 242 rotates. One skilled in the art will appreciate that other viscous fluids or non-Newtonian fluids can be employed without departing from the scope of the present invention.

Prior to completion of the medicament dosage, the spool arm 152 contacts the engaging portion 238 and the rotating arm portion 236 rotates the engaging portion 238 out of engagement with the notch 239, thereby freeing the column assembly 122 to rotate under the influence of the column torsion spring 232. The engagement between the gear portion 142 and the gear 242 of the dampener cartridge 240, however, delays the completion of the rotation of the column assembly 122 until after the completion of the medicament delivery (FIG. 17). At the completion of the rotation of the column assembly (FIG. 18), the column spring 180 drives the column assembly upward.

According to one embodiment, if the energy of column torsion spring 232 is not spent at the completion of the column assembly 122 rotation, the spring 232 expends its remaining energy freely subsequent to the upward movement of the column assembly 122.

Figure 19:
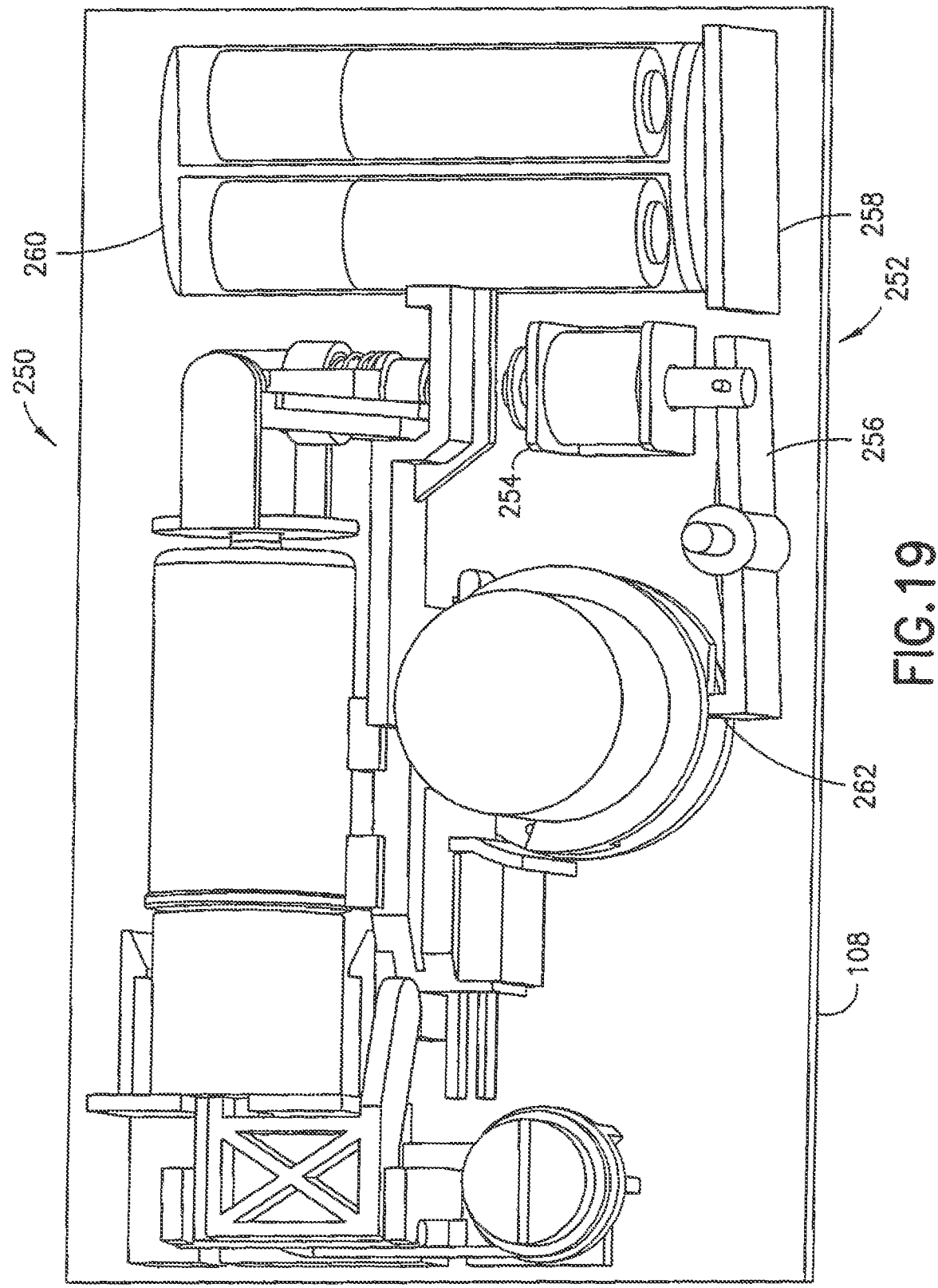
FIGS. 19 and 20 are partial perspective views of a medicament delivery device in accordance with another embodiment of the present invention.
Figure 20:
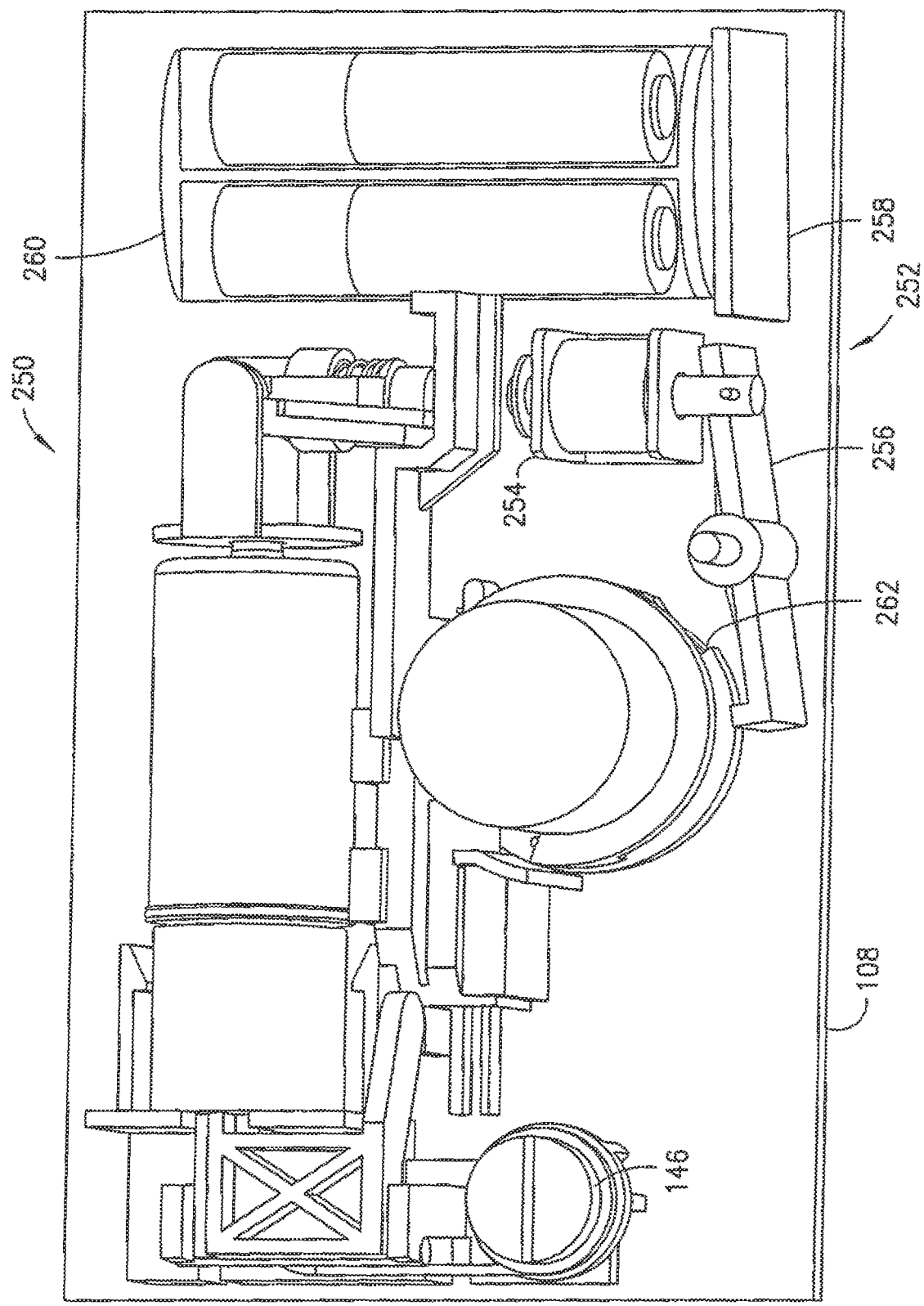

FIGS. 19 and 20 are partial perspective views of a medicament delivery device 250 in accordance with another embodiment of the present invention. In many respects, the device 250 functions substantially similarly to the previously-described device 100. Accordingly, for brevity, redundant description is omitted. In addition to the column spring 180 biasing the column assembly 122 upward, the column assembly 122 includes a column torsion spring (similar to column torsion spring 232, although not shown in FIGS. 19 and 20) rotatably biasing the column assembly 122. Further, the column assembly 122 in the device 250 lacks a gear portion 142 disposed thereon.

The device 250 has a delay mechanism 252 that includes a solenoid 254 and an arm 256 connected to the solenoid 254 and rotatably connected to the base 108. The delay mechanism 252 also includes a controller 258, such as a printed circuit board (PCB), and a portable power source 260. Although depicted as a pair of size AAA batteries, one skilled in the art will appreciate that other portable power sources, such as watch or button batteries, can be employed without departing from the scope of the present invention.

In operation, prior to completion of the medicament dosage, the delay mechanism is activated. Once activated, the controller 258 starts a delay timer. At the expiration of the delay timer, the controller 258 controls the solenoid 254 to disengage the arm 256 from a notch 262 in the column assembly 122, thereby freeing the column assembly 122 to rotate under the influence of the column torsion spring. According to one embodiment, the delay timer does not release the arm from the notch 262 until after the completion of the medicament dosage (FIG. 20), and the rotation of the column assembly 122 is substantially unimpeded.

Additionally, in the depicted embodiment of the device 250, the spool 146 is connected with the controller 258 to input to the controller 258 when the plunger 118 has displaced by a predetermined amount. One skilled in the art will appreciate, however, that other devices may be used to create this input without departing from the scope of the present invention. For example, an optical sensor can be employed such that when the stopper 112 breaks a light beam, the controller 258 starts the delay timer. As another example, a pressure sensor may be employed within the medicament container 110. As a further example, magnets or an RFID chip may be employed on the plunger to detect when the plunger 118 passes a predetermined position, to then signal the controller 258 to start the delay timer. One skilled in the art will also appreciate that the actual delay of the delay timer can vary based on the particular sensor or input selected for the device 250.

Figure 21:
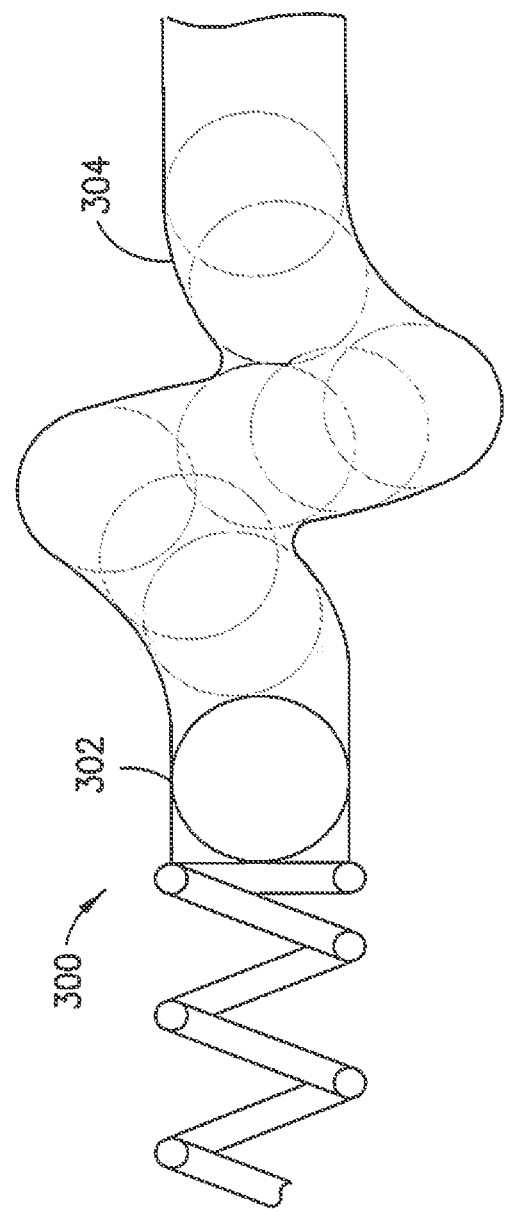
FIG. 21 illustrates a delay mechanism in accordance with another embodiment of the present invention.

FIG. 21 illustrates another embodiment of a delay mechanism. In this embodiment, once the plunger passes a predetermined displacement, a follower 302 is released and is constrained to follow an elongated path 304. That is, the elongated path 304 is longer than the path followed by the plunger. Therefore, the arrival of the follower 302 at the end of the elongated path 304 triggers a subsystem and provides a delay relative to the completion of the plunger stroke.

Figure 22:
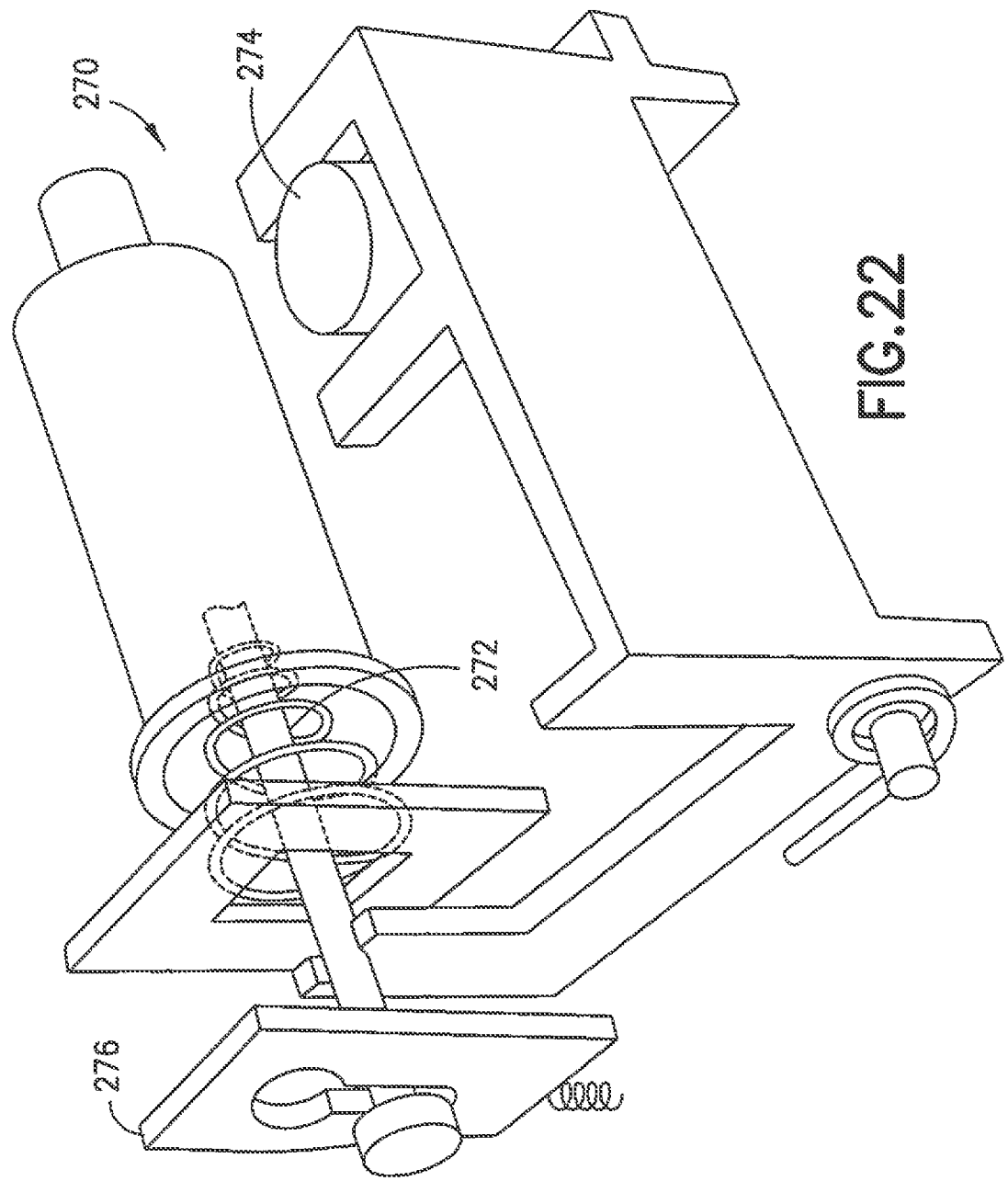
FIG. 22 is a partial perspective view of a medicament delivery device in accordance with another embodiment of the present invention.

FIG. 22 is a partial perspective view of a medicament delivery device 270 in accordance with another embodiment of the present invention. In this embodiment, the plunger 272 is spring-loaded. Additionally, rather than being connected with the column assembly 274, the activation button (not shown) is connected with a spring-loaded keyhole plate 276. When the activation button is depressed by the user, the keyhole plate 276 moves downward until the plunger is permitted to pass therethrough.

According to one embodiment, the needle protection and the end-of-dose indicator are separate. For example, the user may activate a needle protection mechanism after an end-of-dose indicator becomes visible.

Figure 23:
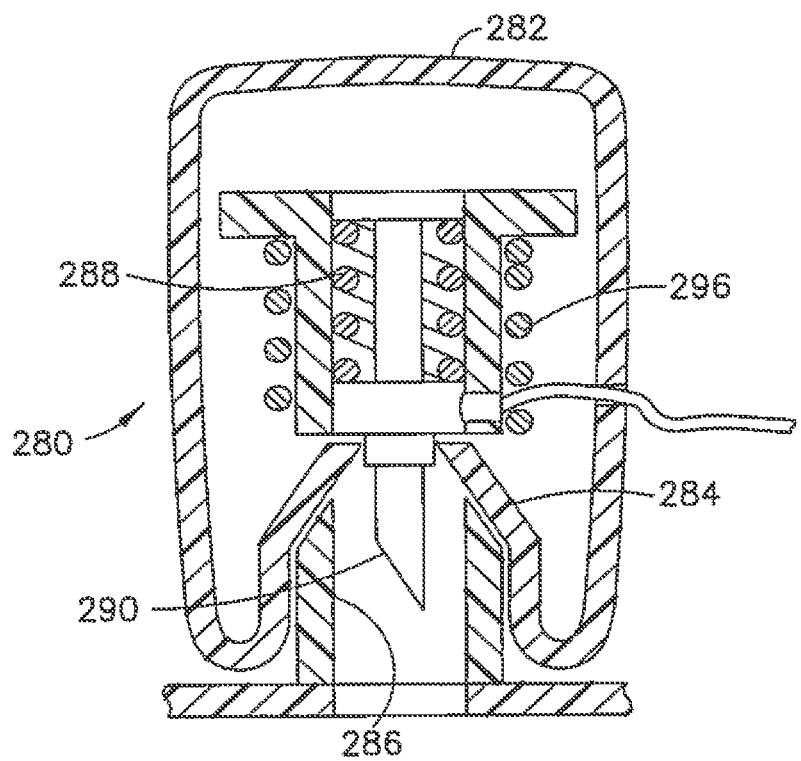
FIGS. 23 and 24 illustrate alternative column assemblies in accordance with further embodiments of the present invention.
Figure 24:
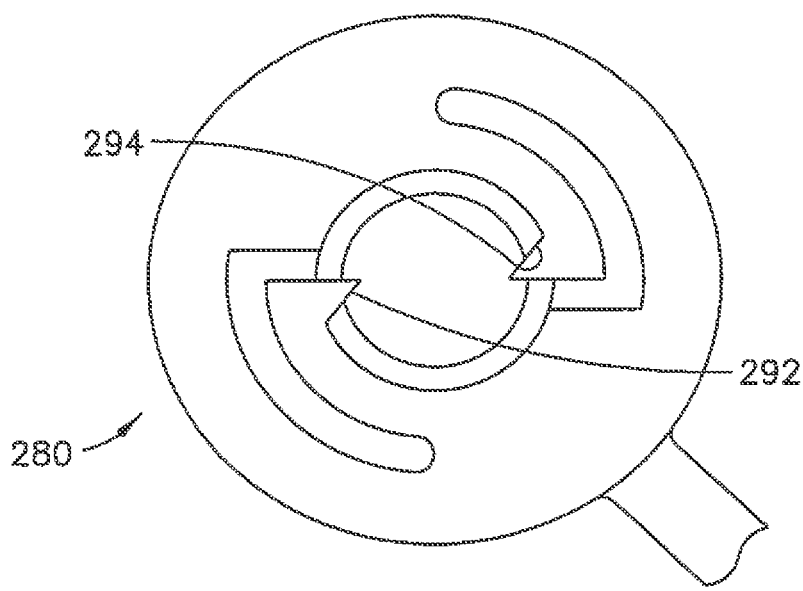
Figure 26:
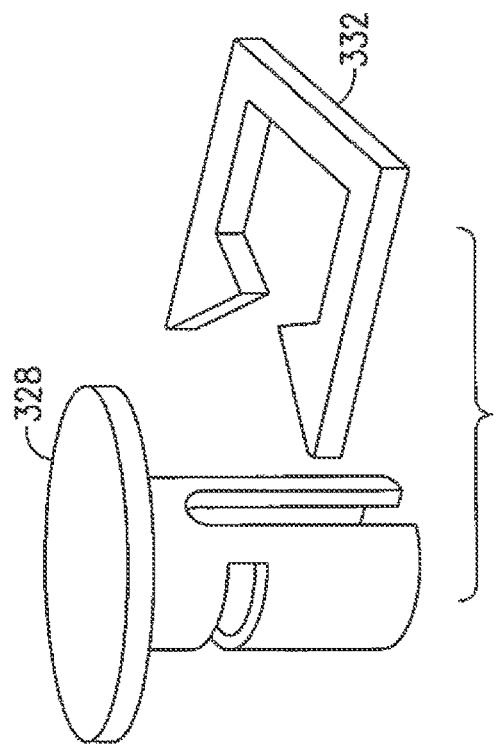
FIGS. 25-28 illustrate a column assembly in accordance with another embodiment of the present invention.
Figure 27:
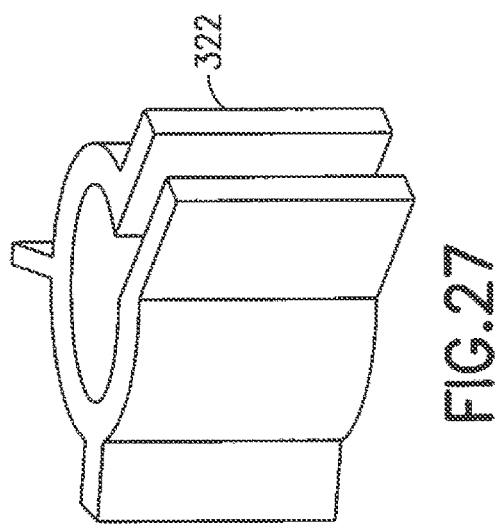
Figure 25:
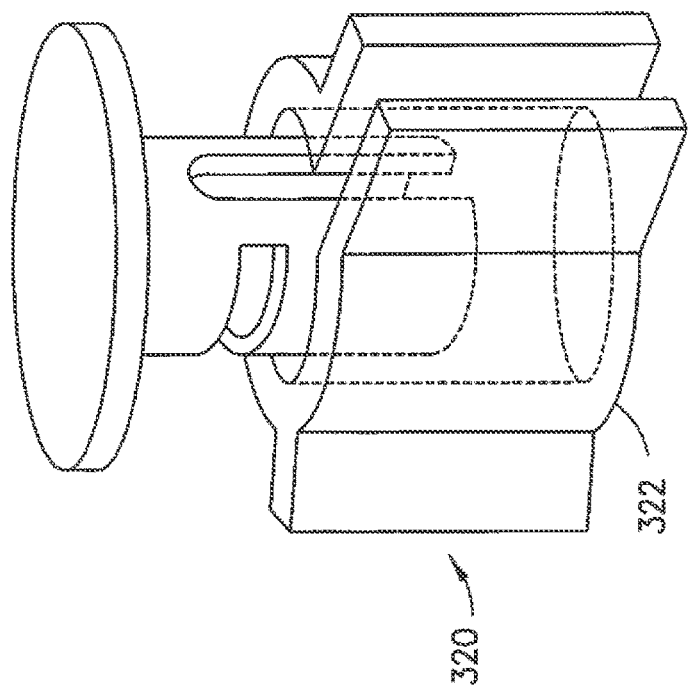
Figure 28:
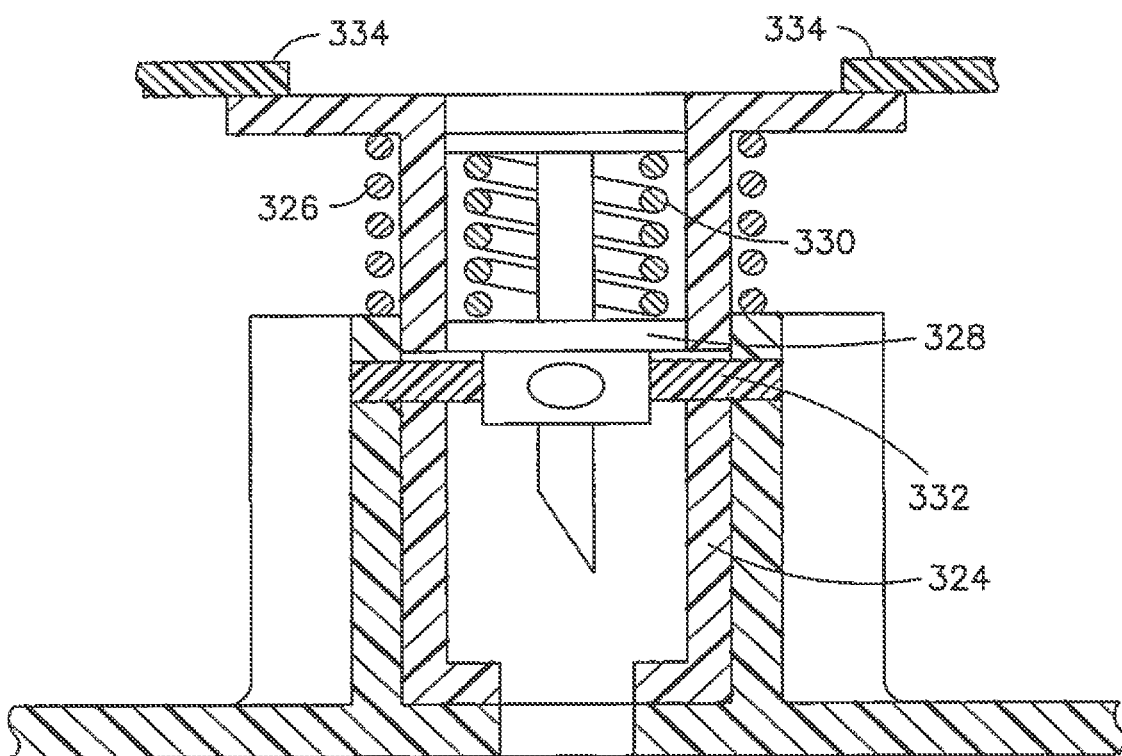

FIGS. 23 and 24 illustrate an alternative embodiment of a column assembly 280. As shown in FIG. 23, when the user depresses the activation button 282, latching fingers 284 are forced radially outward by angled supports 286, thereby permitting an inner spring 288 to drive the needle 290 into the user. Subsequently, as shown in FIG. 24, rotation of the column assembly 280 forces retaining fingers 292 radially outward because of contact with ramped surfaces 294. This action permits the outer spring 296 (see FIG. 23) to drive the column assembly 280 upward.

FIGS. 25-28 illustrate a column assembly 320 in accordance with another embodiment of the present invention. The column assembly 320 includes a column support structure 322 having a plurality of radially outward protruding ribs, and a needle motion column 324 disposed within the column support structure 322 and biased upward by an outer spring 326 that is supported on the protruding ribs. The column assembly 320 also includes a needle hub 328 disposed within the needle motion column 324 and biased downward by an inner spring 330. A retention clip 332 selectively prevents downward displacement of the needle hub 328. The column assembly 320 further includes needle column retention tabs 334 (see FIG. 28).

As the device is activated, the retention clip 332 is removed, permitting the inner spring 330 to drive the needle hub 328 (and thus, the needle) downward into the user's skin. To retract the needle, the needle column retention tabs 334 are removed, thereby permitting the outer spring 326 to drive the needle motion column 324 upward, which also lifts the needle hub 328 upward. As an alternative, the function or placement of the inner and outer springs 330 and 326 can be reversed.

Figure 29:
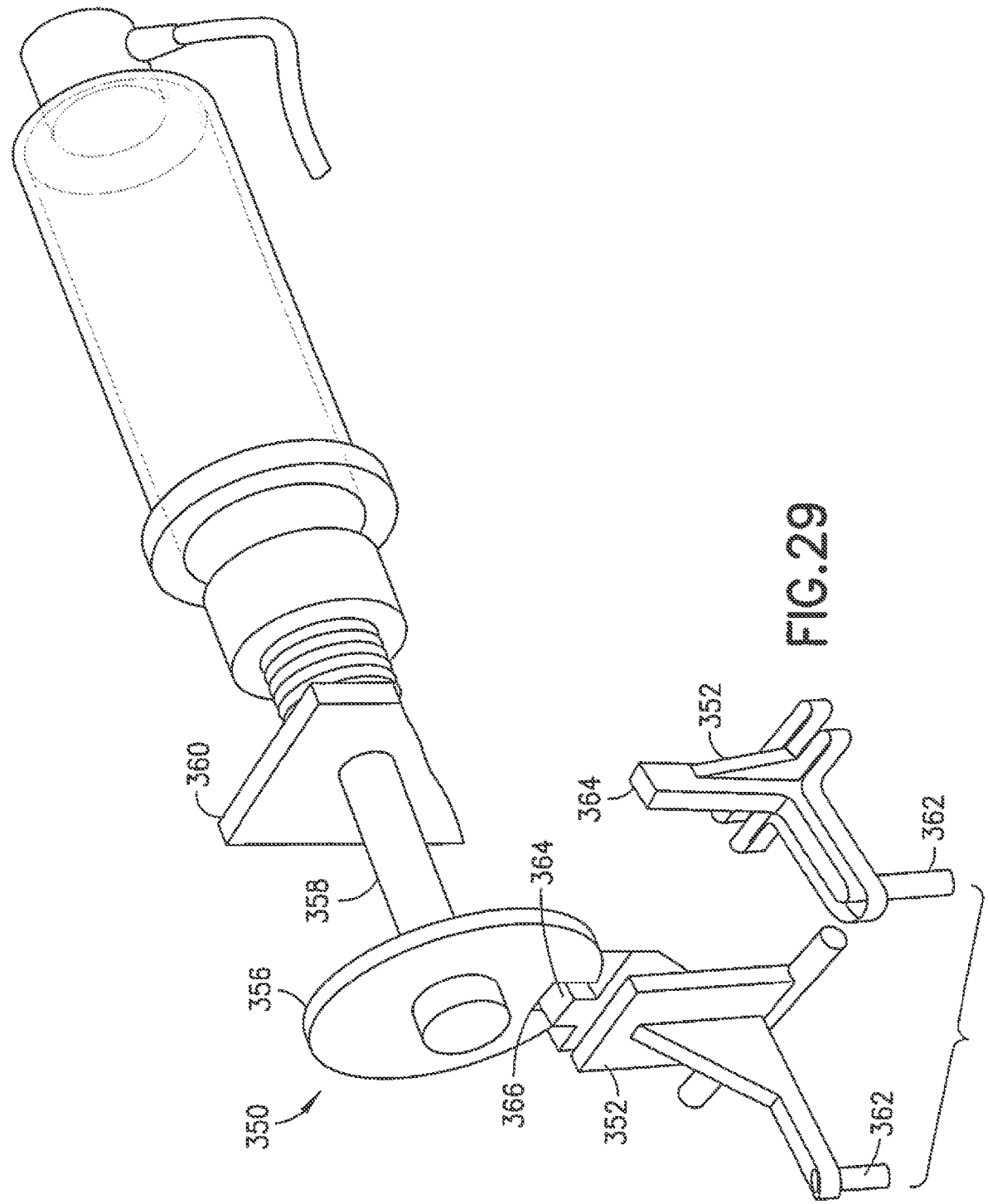
FIG. 29 illustrates an activation mechanism in accordance with another embodiment of the present invention.

FIG. 29 illustrates an activation mechanism 350 in accordance with an embodiment of the present invention. The activation mechanism 350 includes a lockout member 352, a rotationally biased rotary actuator 356 connected with a plunger 358, and a bulkhead 360. The lockout member 352 is rotatably connected with a base. According to one embodiment, the lockout member 352 rotates on a pin relative to the base. According to another embodiment, the lockout member 352 is cantilevered from the base and flexes or deforms to rotate relative to the base. The lockout member 352 includes a lockout pin 362 disposed at one end thereof and protruding through the base. The lockout member 352 also includes a lockout tab 364 at another end thereof. The lockout tab 364 selectively fits in a notch 366 in the rotary actuator 356.

In operation, when the device is placed on the user's skin, the skin forces the lockout tab 362 upward, thereby rotating the lockout member 352. This rotation moves the lockout tab 364 out of engagement with the notch 366 of the rotary actuator 356. The rotation of the rotary actuator 356 rotates the plunger until a shaped portion of the plunger aligns with a corresponding shaped through hole in the bulkhead, at which time the plunger begins displacing relative to the medicament container under the influence of a pressurization spring.

Embodiments of the invention include a delay mechanism for triggering subsystems and/or operations, such as an end-of-dose indication, needle protection, or valve closure. The delay mechanism is activated prior to the completion of medicament delivery. After the medicament delivery has been completed, the delay triggers the next subsystem or operation. The delay mechanism can be mechanical, electrical, electronic, and/or chemical in nature.

In a medicament delivery system or device that has multiple interactions, there are dimensional tolerances that create a tolerance window for when the complete medicament dose has been delivered. There are circumstances where it is beneficial to have a delay after the medicament delivery. To make the end-of-dose indication accurate and transparent to the user of the device, it should to be triggered automatically. Because there is a tolerance window, however, the delay for the end-of-dose indicator needs to be triggered prior to the dose completion, so that the delay will guarantee that the full dose will be delivered, and subsequently, the delay mechanism will trigger the end-of-dose indicator.

Additionally, needle protection can be initiated after a delay that provides enough time to give a high confidence that the medicament delivery has been completed. The user does not want the needle protection to activate prior to complete dose delivery. This could lead to the medicament leaking onto the skin. Additionally, the patient might not know if the complete dose was delivered. Also, if a needle protection device is pushed against the skin while still delivering the dose, it could push a short needle out of the skin inadvertently. Passive needle protection is ideal because the user does not have to perform any additional actions. In a home setting, if a patient takes the medicament delivery system off the skin and a needle is still protruding, then a delayed passive needle protection would still cover the needle without user input. Another advantage to a delay for needle protection is that the needle can be retracted back into the device after medicament delivery is complete.

There are situations where a drug delivery system can have one subsystem or coupled subsystems that are linked to the delay mechanism. For example, the end of dose indication subsystem can be coupled to the needle protection subsystem. The delay can trigger the end of dose indication and the needle protection subsystem.

Further, there can be independent subsystems, such as an end of dose indication (perhaps electronic) that is not triggered by the delay mechanism. In such an embodiment, the delay triggers the needle protection at some point after the end of dose indication has activated. The device may have already been removed from the body when the needle protection activates.

By implementing a delay mechanism that is activated prior to the completion of the dose, the delay mechanism can be timed such that the downstream subsystem (for example, end of dose indication, and/or valve closure, and/or needle protection) is only activated after the completion of the dose delivery. For example, a first trigger that is activated by the drug delivery can activate the time delay. A second trigger can be the end of the time delay and can activate the downstream subsystem.

While the embodiments shown and described are related to medicament delivery devices that deliver medicaments over an extended period of time, one skilled in the art will understand that embodiments of the present invention can also be incorporated into pen injectors, autoinjectors, or the like. Also, while only certain mechanical and electromechanical delay mechanisms are described, it will be understood that any type of mechanical, electromechanical, electrical, electronic, and/or chemical delay mechanism may be used in the practice of the present invention.

Although only a few embodiments of the present invention have been shown and described, the present invention is not limited to the described embodiments. Instead, it will be appreciated by those skilled in the art that changes may be made to these embodiments without departing from the principles and spirit of the invention, the scope of which is defined by the appended claims and their equivalents.

What is claimed is:

1. A method of delivering a medicament, the method comprising:
    receiving an activation command from depression of an activation button;
    in response to receiving the activation command, releasing a biased sliding bracket that travels and releases an ejection mechanism to eject the medicament from a container;
    subsequent to ejecting a portion of the medicament from the container and prior to ejecting substantially all of the medicament from the container, activating a delay mechanism;
    subsequent to ejecting substantially all of the medicament from the container and a predetermined time delay after activation of the delay mechanism, automatically activating an end-of-dose indicator and automatically activating a needle safety mechanism;
    wherein the sliding bracket also opens a valve.

2. The method according to claim 1, wherein the ejection mechanism comprises a biased plunger.

3. The method according to claim 1, wherein the sliding bracket also triggers insertion of a patient needle.

4. A method of delivering a medicament, the method comprising:
    receiving an activation command from depression of an activation button;
    in response to receiving the activation command, releasing a biased sliding bracket to travel a predetermined distance and subsequently release an ejection mechanism to eject the medicament from a container;
    subsequent to ejecting a portion of the medicament from the container and prior to ejecting substantially all of the medicament from the container, activating a delay mechanism;
    subsequent to ejecting substantially all of the medicament from the container and a predetermined time delay after activation of the delay mechanism, automatically initiating an end-of-dose indication and needle shielding.

5. A method of delivering a medicament, the method comprising:
    receiving an activation command;
    in response to receiving the activation command, releasing an ejection mechanism to eject the medicament from a container;
    subsequent to ejecting a portion of the medicament from the container and prior to ejecting substantially all of the medicament from the container, activating a delay mechanism;
    subsequent to ejecting substantially all of the medicament from the container and a predetermined time delay after activation of the delay mechanism, automatically initiating needle shielding, and closure of a valve disposed between the container and a patient needle.

6. A method of delivering a medicament, the method comprising:
    receiving an activation command from depression of an activation button;
    in response to receiving the activation command, releasing a plunger to travel in a first direction to eject the medicament from a container;
    subsequent to ejecting a portion of the medicament from the container and prior to ejecting substantially all of the medicament from the container, activating a delay mechanism;
    subsequent to ejecting substantially all of the medicament from the container and a predetermined time delay after activation of the delay mechanism, automatically activating an end-of-dose indicator and automatically activating a needle safety mechanism to withdraw a needle in a second direction not parallel to the first direction.

7. A method of delivering a medicament, the method comprising:
    receiving an activation command from depression of an activation button;
    in response to receiving the activation command, triggering insertion of a patient needle in a first direction and releasing a plunger to travel in a second direction not parallel to the first direction to eject the medicament from a container;

subsequent to ejecting a portion of the medicament from the container and prior to ejecting substantially all of the medicament from the container, activating a delay mechanism;

subsequent to ejecting substantially all of the medicament from the container and a predetermined time delay after activation of the delay mechanism, automatically activating an end-of-dose indicator and automatically activating a needle safety mechanism.

8. A method of delivering a medicament, the method comprising:

receiving an activation command from depression of an activation button;

in response to receiving the activation command, releasing a sliding bracket biased by a first biasing member to travel and release an ejection mechanism biased by a second biasing member to eject the medicament from a container;

subsequent to ejecting a portion of the medicament from the container and prior to ejecting substantially all of the medicament from the container, activating a delay mechanism;

subsequent to ejecting substantially all of the medicament from the container and a predetermined time delay after activation of the delay mechanism, automatically activating an end-of-dose indicator and automatically activating a needle safety mechanism.

9. A method of delivering a medicament, the method comprising:

receiving an activation command from depression of an activation button;

in response to receiving the activation command, releasing a sliding bracket biased by a first biasing member to travel and release a needle biased by a second biasing member to displace the needle;

subsequent to ejecting a portion of the medicament from a container and prior to ejecting substantially all of the medicament from the container, activating a delay mechanism;

subsequent to ejecting substantially all of the medicament from the container and a predetermined time delay after activation of the delay mechanism, automatically activating an end-of-dose indicator and automatically activating a needle safety mechanism.

\* \* \* \* \*

UNITED STATES PATENT AND TRADEMARK OFFICE
CERTIFICATE OF CORRECTION

| | | |
|---|---|---|
| PATENT NO. | : 11,464,911 B2 | Page 1 of 1 |
| APPLICATION NO. | : 16/258133 | |
| DATED | : October 11, 2022 | |
| INVENTOR(S) | : Krijger et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 144 days.

Signed and Sealed this
Eighth Day of October, 2024

Katherine Kelly Vidal
*Director of the United States Patent and Trademark Office*